(12) United States Patent
Hagewiesche et al.

(10) Patent No.: US 8,008,447 B2
(45) Date of Patent: Aug. 30, 2011

(54) CRYSTALLIZATION OF ANTIBODY OR FRAGMENT THEREOF

(75) Inventors: Annette Marie Clasen Hagewiesche, Carlsbad, CA (US); Julie Fukami, Woodside, CA (US); Mary E. M. Cromwell, Redwood City, CA (US); Rachel Bulotsky Dinges, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 105 days.

(21) Appl. No.: 11/572,369

(22) PCT Filed: Jul. 22, 2005

(86) PCT No.: PCT/US2005/026017
§ 371 (c)(1),
(2), (4) Date: Mar. 6, 2007

(87) PCT Pub. No.: WO2006/012500
PCT Pub. Date: Feb. 2, 2006

(65) Prior Publication Data
US 2007/0258975 A1    Nov. 8, 2007

Related U.S. Application Data

(60) Provisional application No. 60/590,707, filed on Jul. 23, 2004.

(51) Int. Cl.
*C07K 16/00* (2006.01)
*C12P 21/08* (2006.01)
*G01N 31/00* (2006.01)

(52) U.S. Cl. ........................... 530/388.1; 436/4
(58) Field of Classification Search ............ None
See application file for complete search history.

(56) References Cited

U.S. PATENT DOCUMENTS

| 5,608,038 A | 3/1997 | Eibl et al. | |
|---|---|---|---|
| 2004/0006208 A1* | 1/2004 | Karpusas et al. | 530/350 |
| 2004/0133357 A1 | 7/2004 | Zhong et al. | |

FOREIGN PATENT DOCUMENTS

| WO | WO 91/09943 | 7/1991 |
|---|---|---|
| WO | WO 99/55310 | 11/1999 |
| WO | WO 02/30463 A2 | 4/2002 |
| WO | WO 02/072636 A2 | 9/2002 |
| WO | WO 2004/091658 A1 | 11/2004 |

OTHER PUBLICATIONS

Stura et al. Acta Crystallographica Section D. Oct. 2002, part 1, D58:1740-43.*
Cho et al Nature, 2003, 421:756-7601.*
Nguyen et al. Nature Structure Biology, 2003, 10(12):1019-25.*
Ahamed et al. "Phase Behaviour of Intact Monoclonal Antibody", Biochemical Journal, Jul. 2007, vol. 93, pp. 610-619.*
Navia et al. "Crystal structure of galactan-binding mouse immunoglobulin J539 Fab at 4.5-Å resolution." *Proc. Natl. Acad. Sci. USA.* vol. 76, No. 8. Aug. 1979. pp. 4071-4074.
Huang et al. "Three quaternary structures for a single protein." *Proc. Natl. Acad. Sci. USA.* vol. 93. Jul. 1996. pp. 7017-7021.
Chang et al. "Novel Arrangement of Immunoglobulin Variable Domains: X-ray Crystallographic Analysis of the λ-Chain Dimer Bence-Jones Protein Loc." *Biochemistry* vol. 24. 1985. pp. 4890-4897.
Yang et al. "Crystalline monoclonal antibodies for subcutaneous delivery." *PNAS.* vol. 100, No. 12. Jun. 10, 2003. pp. 6934-6939.
Cudney et al. "Screening and Optimization Strategies for Macromolecular Crystal Growth." *Acta Crystallographica Section D.* vol. 50. 1994. pp. 414-423.
Harris et al. "Crystallization of Intact Monoclonal Antibodies." *Proteins: Structure, Function, and Genetics.* vol. 13. 1995. pp. 285-289.
Stura et al. "Reverse Screening." *Acta Crysallographica Section D.* vol. 50. 1994. pp. 448-455.
Muller et al. "VEGF and the Fab fragment of a humanized neutralizing antibody: crystal structure of the complex at 2.4. Å resolution and mutational analysis of the interface." *Structure.* vol. 6, No. 9. 1998. pp. 1153-1167.
Chen et al. "Selection and Analysis of an Optimized Anti-VEGF Antibody: Crystal Structure of an Affinity-matured Fab in Complex with Antigen." *J. Mol. Biol.* vol. 293, No. 4. 1999. pp. 865-881.
Ferrara et al. "Discovery and Development of Bevacizumab, an Anti-VEGF antibody for treating cancer." *Nature Reviews: Drug Discovery.* vol. 3. May 2004. pp. 391-400.
Cleland et al. "The Development of Stable Protein Formulations: A Close Look at Protein Aggregation, Deamidation, and Oxidation." *Crit. Rev. in Thera. Drug Carrier Systems.* vol. 10, No. 4. 1993. pp. 307-377.

\* cited by examiner

*Primary Examiner* — Suzanne M. Noakes
(74) *Attorney, Agent, or Firm* — Irene Pleasure; Christopher De Vry; Arnold & Porter LLP

(57) ABSTRACT

The present disclosure concerns methods of crystallization and/or concentration of antibody or antibody fragments. The methods comprise contacting an antibody or antibody fragment with a solution comprising a salt of a divalent cation. Crystals and/or protein gels of antibody or antibody fragments are useful in compositions and formulations.

13 Claims, 8 Drawing Sheets

CRYSTALLIZATION OF ANTIBODY OR FRAGMENT THEREOF

CROSS REFERENCE TO RELATED APPLICATION

This application is a 371 application of International Application PCT/US2005/26017, filed Jul. 22, 2005, which application claims the benefit of U.S. Application Ser. No. 60/590,707 filed Jul. 23, 2004 under 35 U.S.C. §119(e), which applications are hereby incorporated by reference.

BACKGROUND OF THE INVENTION

Monoclonal antibodies are becoming powerful therapeutic agents in the treatment of a number of diseases and conditions, including but not limited to cancer, respiratory diseases, inflammatory diseases, and infectious diseases. Generally, therapies that include antibodies require the delivery of between 100 mg and 1 g of antibody per dose. A commonly used approach for such treatments is to use intravenous infusions of from about 2 to 20 mL of a 50 mg/mL solution of the antibody. Because introduction methods other than intravenous administration, such as subcutaneous injection, are desired, it would be advantageous to have more concentrated solutions of the antibodies. However, concentrated solutions of antibodies can lead to problems, including but not limited to, highly viscous solutions, protein aggregation, and problems with the stability of the solutions.

Fragments of antibodies have been crystallized, for example, for use in X ray crystallography. Previously reported methods of crystallizing monoclonal antibodies have generally used the vapor diffusion technique. Drawbacks of this technique include the minute quantities of crystals that are produced, and the use of agents that in some cases are unacceptable for use in humans. Batch-process methods can also be used to produce slightly larger quantities of crystals. Commonly used batch-process methods typically utilize organic or polymeric precipitants. Protocols that utilize organic precipitants for crystallizing antibodies have been described. Yang et al., PNAS, vol. 100, no. 12, pp. 6934-6939 (2003); Kuznetsov et al., J. Crystal Growth, vol. 232, pp. 30-39 (2001); Kuznetsov et al., J. Structural Biology, vol. 131, pp. 108-115 (2000); Harris et al., Immunological Reviews, vol. 163, pp. 35-43 (1998); Harris et al., J. Mol. Biol., vol. 275, pp. 861-872, (1998); and Harris et al., Proteins, vol. 23, pp. 285-89 (1995). Examples of commonly used organic or polymeric precipitants include polyethylene glycol (PEG), isopropanol, Jeffamine® (Huntsman Petrochemical Corp., Salt Lake City, Utah), and (+/−)-2-methyl-2,4-pentanediol (MPD).

As many antibodies are now processed on a large scale for administration to humans, it is desirable to have methods of forming crystals and/or concentrated protein gels on a large scale, especially those that do not include organic or polymeric precipitants. The crystals and/or gels are useful for storage and administration therapeutically.

SUMMARY OF THE INVENTION

One aspect of the invention provides a method for producing crystals of an antibody or fragment thereof that includes the steps of contacting an antibody or fragment thereof with a solution that includes about 1 to 500 millimolar (mM) of a salt of a divalent cation and about 1 to 100 mM buffer, and incubating the antibody or fragment thereof and the solution until crystals of the antibody or fragment thereof are formed.

In some embodiments, a method comprises contacting an antibody or fragment thereof with a solution that comprises about 1 to 120 mM zinc salt; and incubating the antibody or fragment thereof and the solution until crystals and/or a protein gel of the antibody or fragment thereof are formed. In some embodiments, incubation is at ambient temperatures. In some embodiments, the temperature is from about 20 to 27° C. In other embodiments, incubation is at less than a temperature of about 20° C., preferably from about 0 to 20° C., more preferably about 0 to 10° C.

In some embodiments, a method comprises contacting an antibody or fragment thereof with a solution that consists essentially of a zinc salt and a buffer; and incubating the antibody or fragment thereof and the solution until crystals and/or a protein gel of the antibody or fragment thereof are formed.

A method for producing crystals of an antibody or fragment thereof includes contacting an antibody or fragment thereof with a solution that includes a zinc salt and lacks other precipitants; and incubating the antibody or fragment thereof and the solution until crystals of the antibody or fragment thereof are formed.

In some embodiments, the divalent salt is about 10 to 80 mM, more preferably 25 mM to 60 mM, zinc chloride ($ZnCl_2$). In other embodiments, the buffer is about 1 to 20 mM NaOAc, more preferably about 25 to 75 mM sodium acetate (NaOAc). In some embodiments, the solution comprises more than about 10 mM $ZnCl_2$ and more than about 5 mM NaOAc. For example, the solution comprises about 100 mM $ZnCl_2$ and about mM NaOAc. In other embodiments, the buffer has a pH of about 4 to about 9, more preferably about 4.7 to 5.7.

Also provided is a crystal of an antibody or fragment thereof produced by the methods described herein. The antibodies can be a polyclonal antibody, monoclonal antibody, chimeric antibody, bispecific antibody, human antibody, or humanized antibody.

The invention also provides a composition including a crystal or a protein gel of antibody selected from the group consisting of anti-VEGF antibody, anti-CD20, anti-CD11a, anti-CD40, anti-Apo-2, anti-HER2, anti-IgE, and fragments thereof, and a carrier. Preferably, the antibodies are full-length glycosylated antibodies.

Also provided is a formulation that includes a crystal or protein gel of an antibody selected from the group consisting of anti-VEGF, anti-Apo-2, anti-CD20, anti-CD11a, anti-CD40, anti-HER2, anti-Apo-2, anti-IgE, and fragments thereof, and at least one ingredient.

The invention also provides a method for treating a condition in a mammal comprising administering to the mammal an effective amount of one of the above compositions or formulations. The conditions include those that are associated with VEGF, CD20, CD11a, CD40, Apo-2, and HER2.

An article of manufacture is also provided that includes at least one of the above compositions or formulations and a container.

The invention provides methods, compositions, and formulations, useful, inter alia, to concentrate, purify, store and deliver antibodies or fragments thereof.

DETAILED DESCRIPTION OF THE PREFERRED EMBODIMENT

Detailed Description

Definitions

Figure 1:
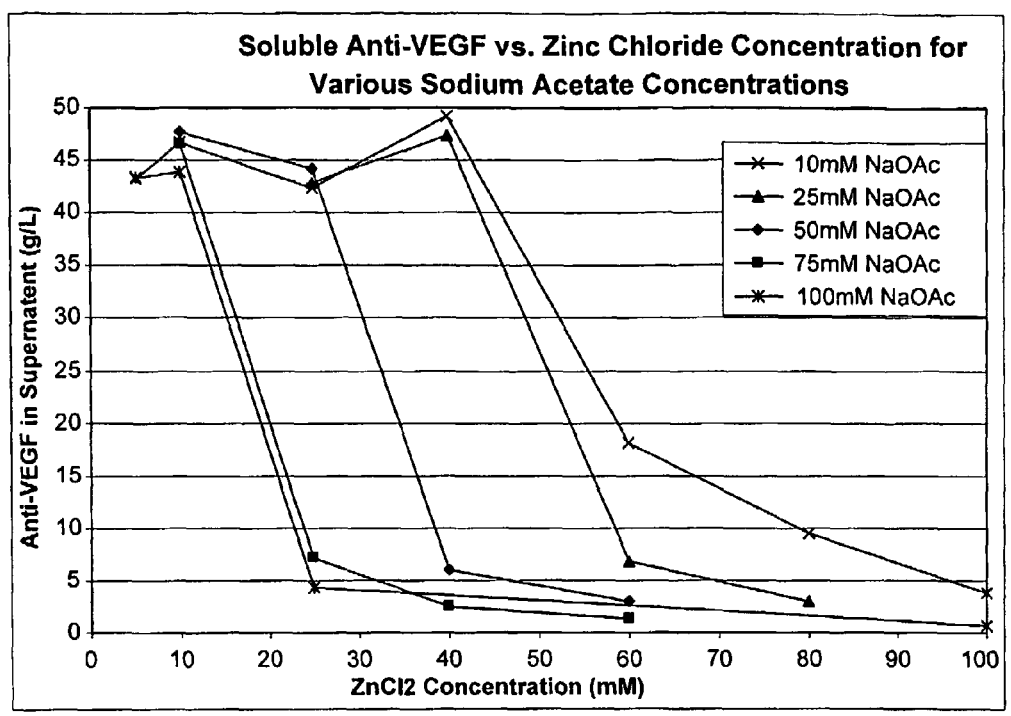
FIG. 1 is a graph showing the solubility of anti-VEGF in varying concentrations of $ZnCl_2$ and NaOAc, pH 5.7, room temperature. The graph shows the concentration of soluble anti-VEGF plotted as a function of $ZnCl_2$ concentration and NaOAc concentrations. Different NaOAc concentrations are shown as follows: × 10 mM NaOAc; Δ 25 mM NaOAc (white line); ♦ 50 mM NaOAc; ■ 75 mM NaOAc; * 100 mM NaOAc.

The terms "antibody" and "immunoglobulin" are used interchangeably in the broadest sense and include monoclonal antibodies (full-length or intact monoclonal antibodies), polyclonal antibodies, antibody compositions with polyepitopic specificity, affinity matured antibodies, humanized antibodies, human antibodies, chimeric antibodies, humanized, multivalent antibodies, and multispecific antibodies (e.g., bispecific antibodies so long as they exhibit the desired biological activity) as well as antigen binding fragments (e.g., Fab, $F(ab')_2$, scFv and Fv), so long as they exhibit the desired biological activity.

A full-length antibody comprises four polypeptide chains, two identical heavy (H) chains and two identical light (L) chains inter-connected by disulfide bonds. Each heavy chain is comprised of a heavy chain variable region domain ($V_H$) and a heavy chain constant region. The heavy chain constant region is comprised of three domains, CH1, CH2 and CH3. Each light chain is comprised of a light chain variable region domain ($V_L$) and a light chain constant region domain. The light chain constant region is comprised of one domain, $C_L$. The $V_H$ and $V_L$ domains can be further subdivided into complementarity regions (CDRs) or hypervariable loops (HVLs), interspersed with regions that are more conserved, termed framework regions (FR). Each $V_H$ and $V_L$ is typically composed of three CDRs and four FRs, arranged from amino-terminus to carboxy-terminus in the following order: FR1, CDR1, FR2, CDR2, FR3, CDR3, FR4.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al., *Cellular and Mol. Immunology*, 4th ed. (2000). An antibody may be part of a larger fusion molecule, formed by covalent or non-covalent association of the antibody with one or more other proteins or peptides.

The light chains of antibodies from any vertebrate species can be assigned to one of two clearly distinct types, called kappa (κ) and lambda (λ), based on the amino acid sequences of their constant domains.

The term "full-length antibody" refers to an antibody in its substantially intact form including at least 2 heavy and 2 light chains, not antibody fragments as defined below. The term particularly refers to an antibody with heavy chains that contain Fc region. A full-length antibody can be a native sequence antibody or a recombinant antibody. A full-length antibody can be human, humanized and/or affinity matured.

The term "monoclonal antibody" as used herein refers to an antibody obtained from a population of substantially homogeneous antibodies, i.e., the individual antibodies comprising the population are essentially identical except for variants that may arise during production of the antibody.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from a non-human immunoglobulin. For the most part, humanized antibodies are human immunoglobulins (recipient antibody) in which residues from a CDR or hypervariable loop (HVL) of the recipient are replaced by residues from a CDR or HVLs of a non-human species (donor antibody) such as mouse, rat, rabbit or nonhuman primate having the desired specificity, affinity, and capacity. In some instances, framework region (FR) residues of the human immunoglobulin are replaced by corresponding non-human residues to improve antigen binding affinity. Furthermore, humanized antibodies may comprise residues that are not found in the recipient antibody or the donor antibody. These modifications may be made to improve antibody affinity or functional activity. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. Humanized antibodies can also be produced as antigen binding fragments as described herein. The humanized antibody optionally will also comprise at least a portion of an immunoglobulin constant region (Fe), typically that of or derived from a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech* 5:428-433 (1994).

A "human antibody" is one which possesses an amino acid sequence which corresponds to that of an antibody produced by a human and/or has been made using any of the techniques for making human antibodies. This definition of a human antibody specifically excludes a humanized antibody comprising non-human antigen binding residues.

An "affinity matured" antibody is one with one or more alterations in one or more hypervariable regions which result in an improvement in the affinity of the antibody for antigen, compared to a parent antibody which does not possess those alteration(s). Preferred affinity matured antibodies will have nanomotar or even picomolar affinities for the target antigen. Affinity matured antibodies are produced by procedures known in the art. Marks et al., *Bio/Technology* 10:779-783 (1992) describes affinity maturation by VH and VL domain shuffling. Random mutagenesis of CDR and/or framework residues is described by: Barbas et al., *Proc. Nat. Acad. Sci. USA* 91:3809-3813 (1994); Scier et al., *Gene* 169:147-155 (1995); Yelton et al., *J. Immunol.* 155:1994-2004 (1995); Jackson et al., *J. Immunol.* 154(7):3310-9 (1995); and Hawkins et al., *J. Mol. Biol.* 226:889-896 (1992).

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains having one interchain disulfide bond between the heavy and light chain; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) hingeless antibodies including at least VL, VH, CL, CH1 domains and lacking hinge region; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd segments (VH-CH1-VH-CH1) which, together with complementary light chain polypeptides, form a pair of antigen binding regions.

As used herein, "crystal" refers to one form of a solid state of matter in which atoms are arranged in a pattern that repeats periodically in three dimensions, typically, forming a lattice.

As used herein, "gel" refers to a concentrated form of antibody or antibody fragment that is a viscoelastic solution that is more solid than a liquid colloidal solution. Optionally, the gels may comprise crystals. Gels that are formed using methods of the invention generally contain a high concentration of antibody or fragments thereof and may, optionally comprise crystals.

"Precipitant" as used herein refers to an agent that causes a compound or molecule to become insoluble. In some cases, the compound or molecule forms a crystal. Precipitants that can be used to form crystals of compounds or molecules are, typically, salts, polymers or organic molecules. Organic precipitants include isopropanol, ethanol, hexanediol, and 2-methyl-2,4-pentanediol (MPD). Polymeric precipitants include polyethylene glycol and polyamines such as Jeffamine®. Salts used include ammonium sulfate, sodium citrate, sodium acetate, ammonium chloride, sodium chloride and magnesium formate, typically at concentrations of 0.2 M or greater.

A "disorder" or "condition" is any condition that would benefit from treatment with the antibody. This includes chronic and acute disorders or diseases including those pathological conditions that predispose the mammal to the disorder in question. Non-limiting examples of disorders to be treated herein include malignant and benign tumors, non-leukemia and lymphoid malignancies; neuronal, glial, astrocytal, hypothalamic and other glandular, macrophagal, epithelial, stromal and blastocoelic disorders; and inflammatory, angiogenic and immunologic disorders.

As used herein, "treatment" refers to clinical intervention in an attempt to alter the natural course of the individual or cell being treated. Desirable effects of treatment include alleviation of symptoms, diminishment of any direct or indirect pathological consequences of the disease, preventing metastasis, decreasing the rate of disease progression, amelioration or palliation of the disease state, and remission or improved prognosis.

Modes for Carrying out the Invention

Antibody and antibody fragments have become very useful, especially therapeutically. Many antibodies are now being investigated for therapeutic use. Therapeutic use often requires large-scale production of antibodies or antibody fragments. One aspect of the invention include a method for concentrating, purifying, and storing antibodies or fragments thereof, especially those produced on a large scale. The methods of the invention provide crystals, gels, and gels with crystals. Crystals and/or gels of antibodies or fragments thereof are useful for example, for characterization of 3-dimensional structure via x-ray diffraction, for storage, for concentration, for purification, and for delivery of antibody or antibody fragment.

Many proteins because of their size and their three-dimensional configurations can be difficult to crystallize. Typically, several combinations of precipitants, buffers and pH must be screened in order to identify the combination of conditions that will provide for crystallization. Antibodies and antibody fragments have been especially difficult to crystallize because of their size and the fact that the hinge region makes the molecule more flexible and less rigid. In addition, antibodies or fragments thereof, can be glycosylated depending on the source of the antibody.

In some embodiments, a method comprises contacting an antibody or fragment thereof with a solution comprising, consisting essentially of, or consisting of a salt of a divalent cation. In some embodiments, the presence of a divalent cation salt is at low concentration, for example, about 1 to 500 mM. A solution also can comprise, consist essentially of, or consist of a buffer, such as sodium acetate. In some embodiments, the buffer has a low ionic strength, for example, about 1 to 100 mM. Examples of divalent cations include, but are not limited to, zinc, magnesium, and calcium. While not meant to limit the invention in any way, the salt of the divalent cation is acting as a precipitant and contributes to protein crystal formation. In some cases, the solution does not include other precipitants, such as organic or polymeric precipitants.

In some embodiments, a method comprises contacting an antibody or fragment thereof with a solution comprising, consisting essentially of, or consisting of a zinc salt. In some embodiments, the presence of a zinc salt is at low concentration, for example, about 1 to 120 mM, preferably 10 to 80 mM, and more preferably 25 to 60 mM. In some embodiments, the zinc salt is $ZnCl_2$. A solution can comprise, consist essentially of, or consist of a buffer, such as sodium acetate. In some embodiments, the buffer has a low ionic strength, for example, about 1 to 100 mM, preferably 1 to 20 mM, and more preferably, 25 mM to 75 mM. In some embodiments, the solution comprises about 100 mM $ZnCl_2$ and about 10 mM NaOAc. In some cases, the solution does not include other precipitants, such as organic or polymeric precipitants. The methods provide for formation of crystals and/or protein gels. Optionally, the protein gels may comprise crystals.

In some embodiments, the solution comprises more than about 10 mM $ZnCl_2$ and more than about 5 mM NaOAc. In other embodiments, the solution comprises 100 mM $ZnCl_2$ and 10 mM NaOAc.

In some embodiments, a method comprises contacting an antibody or fragment thereof with a solution comprising, consisting essentially of, or consisting of a magnesium salt. In some embodiments, magnesium chloride ($MgCl_2$) is utilized at low concentration, for example, about 1 to 500 mM, more preferably about 200 to 500 mM and most preferably about 1 to 100 mM. A solution can comprise, consist essentially of, or consist of a buffer, such as sodium acetate or tris. In some embodiments, the buffer has a low ionic strength, for example, about 1 to 100 mM. In some cases, the solution does not include other precipitants, such as organic or polymeric precipitants. In some cases, the pH of the solution is high, for example from about 7.5 to about 9. The methods provide for formation of crystals and/or protein gels. Optionally, the protein gels may comprise crystals.

In some embodiments, a method comprises contacting an antibody or fragment thereof with a solution comprising, consisting essentially of, or consisting of a zinc salt to form a protein gel. Optionally, protein gels may comprise crystals. In some embodiments, the zinc salt is at a low concentration, for example, about 1 to 120 mM. A solution can comprise, consist essentially of, or consist of a buffer, such as sodium acetate. In some embodiments, the buffer has a low ionic strength, for example, about 1 to 100 mM. In some cases, the solution does not include other precipitants, such as organic or polymeric precipitants.

The methods of the invention provide a low cost way to crystallize, concentrate or purify antibody or antibody fragments. In some cases, the methods of the invention provide methods that do not include the use of other precipitants, such as polymers or organic precipitants that might be undesirable in the product. Crystals and/or protein gels of antibody or antibody fragments can be combined with carriers or other ingredients for storage and/or for administration.

Antibodies or Fragments thereof

Antibody or antibody fragments are used in the methods of the invention. Antibodies include, without limitation, polyclonal, monoclonal antibodies, affinity matured antibodies, antibodies with polyepitopic specificity, humanized antibodies, human antibodies, chimeric antibodies and multispecific antibodies.

In some cases, antibodies are produced as full-length antibodies. Full-length antibodies typically comprise 2 heavy and 2 light chains. There are 5 major classes of immunoglobulins and these include IgA, IgD, IgE, IgG and IgM. Several of these may be further divided into subclasses, such as IgG1, IgG2, IgG3, IgG4, IgM1, IgM2, IgA1 or IgA2. Antibodies of one or more of these classes can be utilized in the methods of the invention. In some embodiments, the antibody is an IgG antibody.

Antibody fragments can also be used in the methods of the invention. Antibody fragments comprise antigen binding fragments and include Fab, Fab', $Fab_2$, $Fab'_2$, Fd, single chain Fv, $scFv_2$, dAb, hingeless antibodies, diabodies, and linear antibodies.

Depending on the source of the antibody or fragment thereof, antibodies may be glycosylated. Typically, recombinant antibodies obtained from or produced in mammalian or insect cells are glycosylated. Antibodies or fragments thereof obtained from or produced in prokaryotic cells lack glycosylation or are aglycosylated. Glycosylation of antibodies may also be modified or eliminated by mutation of glycosylation site sequences.

Antibodies or antibody fragments are specific for an antigen. Antibodies useful in the methods of the invention include antibodies to antigens including molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TP), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNE), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGE); transforming growth factor (TGF) such as TGP-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred antigens for antibodies encompassed by the present invention include CD proteins such as CD3, CD4, CD8, CD19, CD20, CD40, CD34, and CD46; members of the ErbB receptor family such as the EGF receptor, HER2, HER3 or HER4 receptor; cell adhesion molecules such as LFA-1, Mac1, p150.95, VLA-4, ICAM-1, VCAM, $\alpha 4/\beta 7$ integrin, and $\alpha v/\beta 3$ integrin including either $\alpha$ or $\beta$ subunits thereof (e.g. anti-CD11a, anti-CD18 or anti-CD11b antibodies); growth factors such as VEGF; tissue factor (TF); TGF-$\beta$ alpha interferon ($\alpha$-IFN); an interleukin, such as IL-8; blood group antigens; Apo-2 death receptor; flk2/flt3 receptor; obesity (OB) receptor; mpl receptor; CTLA-4; protein C; etc. The most preferred targets herein are VEGF, TF, CD19, CD20, CD40, TGF-$\beta$, CD11a, CD18, Apo-2 death receptor, and C24.

In some embodiments, the antibodies or fragments thereof comprise anti-VEGF, anti-Apo-2, anti-IgE, anti-HER2, anti-CD11a, or anti-CD20.

An antibody or antibody fragments can be obtained from a natural source, prepared synthetically or by recombinant methods. Methods of producing antibodies are known to those of skill in the art and include producing antibody or antibody fragments by phage display. Large-scale production methods are known and include production of antibody or fragments thereof in 10 liter amounts or greater.

Antibody or antibody fragments are purified by methods known to those of skill in the art. In some cases, the antibody or fragment produced is purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing. SDS-PAGE, ammonium sulfate precipitation, and gel filtration using, for example, Sephadex G-75. For example, as the first step of purification, the antibody or fragment thereof derived from the cell culture is applied onto the Protein A immobilized solid phase to allow specific binding of the antibody to Protein A. The solid phase is then washed to remove contaminants non-specifically bound to the solid phase. Finally the antibody is recovered from the solid phase by elution.

In some embodiments of the invention, the concentration of the antibody in the solution used in the methods of the invention is at least 1 g/L. The concentration of the antibody in the solution ranges from about 1 to about 100 g/L. In further embodiments of the invention, the concentration of the antibody ranges from about 20 to about 100 g/L. In yet another embodiment of the invention, the concentration of the antibody ranges from about 40 to about 90 g/L.

Methods

The methods of the invention involve methods of crystallizing or concentrating an antibody or an antibody fragment from solution. Crystals or protein gels are useful, for example, for characterizing the structure of, for storing, for concentrating, for purifying, and for delivery of the antibody or fragment thereof. In some embodiments, the concentration of the antibody being concentrated is at least 1 gm/L., and more preferably, at least 40 to 90 gm/L. The methods of the invention provide a low cost method for producing crystals of antibody or fragments thereof. In one aspect of the invention, a method comprises contacting an antibody or fragment thereof with a solution that comprises, consists essentially of, or consists of a divalent cation salt and incubating the antibody or fragment thereof with the solution until crystals of the antibody or fragment thereof are formed.

In some embodiments, the method comprises contacting an antibody or fragment thereof with a solution that comprises, consisting essentially of or consists of a zinc salt at a concentration of about 1 to about 120 mM, more preferably about 10 to 80 mM and most preferably, about 25 to 60 mM zinc salt. Zinc salts include zinc chloride, zinc phosphate, zinc citrate, zinc acetate, or zinc sulfate. In some embodiments, the solution comprises, consists essentially of or consists of about 1 to about 100 mM $ZnCl_2$. In specific embodiments, the solution comprises more than 10 mM $ZnCl_2$ and more than 5 mM NaOAc, and preferably about 100 mM $ZnCl_2$ and about 10 mM NaOAc. In some embodiments, the method provides a protein gel that may, optionally, comprise crystals.

In some embodiments, the method comprises contacting an anti-VEGF antibody or a fragment thereof with a solution that comprises, consisting essentially of or consists of a magnesium salt at a concentration of about 1 to about 500 mM, more preferably about 200 to 500 mM and most preferably, about 10 to 100 mM magnesium salts. The magnesium salts are those that are soluble and can disassociate in the solvent. Magnesium salts include magnesium chloride, magnesium phosphate, magnesium citrate, magnesium acetate, and magnesium sulfate. In some embodiments, the solution comprises, consists essentially of or consists of about 1 to about 100 mM magnesium chloride. In some embodiments, the solution has a high pH, for example a pH of about 7.5 to about 9.

In some embodiments, the method comprises contacting an anti-VEGF or a fragment thereof with a solution that comprises, consisting essentially of or consists of a calcium salt at a concentration of about 1 to about 500 mM, more preferably about 1 to 200 mM and most preferably, about 10 to 100 mM calcium salts. Calcium salts are those that are soluble and can disassociate in the solvent. The calcium salts include calcium chloride, calcium phosphate, calcium citrate, calcium acetate, and calcium sulfate. In some embodiments, the solution comprises, consists essentially of or consists of about 1 to about 100 mM calcium chloride. In some embodiments, the solution has a high pH, for example a pH of about 7.5 to about 9.

In some embodiments, the method comprises contacting an antibody or fragment thereof with a solution that comprises, consisting essentially of a zinc salt, but lacks other precipitants. In some cases, it may be desirable to minimize the use of other precipitants, such as organic molecules including 2-methyl-2,4-pentanediol, iso-propanol or polymeric compounds, including polyethylene glycols or polyamines.

These embodiments may offer an advantage over prior art crystallization methods because other precipitants are not used. One possible advantage in not using any organic or polymeric precipitants would be economical, i.e., in a large scale operation, for example, the cost of the organic precipitants could be of consequence, so a method that does not use them would be more economically efficient. Another possible advantage to not using any organic precipitants would be that there would not be any residue of the organic precipitant in the final crystals. This could be an advantage due to the desire to use crystallized antibodies to formulate solutions for administration to mammals. Some of the organic precipitants that are used may not be desirable for administering to mammals, such as humans.

Methods of the invention also include a solution that comprises, consists essentially of, or consists of a salt of a divalent cation and a buffer. Buffers that can be used in the invention include any commonly used by those of skill in the art. Examples of which include, but are not limited to, acetic acid, ammonium carbonate, ammonium phosphate, boric acid, citric acid, HEPES (4-(2-hydroxyethyl)-1-piperazineethanesulfonic acid), bicine, MES, sodium cacodylate, imidazole, ammonium chloride, magnesium formate, lactic acid, phosphoric acid, potassium citrate, potassium metaphosphate, potassium phosphate monobasic, sodium acetate, sodium citrate, sodium lactate, dibasic sodium phosphate, monobasic sodium phosphate, and Tris (tris hydroxymethylaminoethane). In some embodiments of the invention, sodium acetate (NaOAc) is used as the buffer.

In some embodiments, the concentration of the buffer in the solution can range from about 1 to about 100 mM. In another embodiment of the invention, the concentration of the buffer in the solution can range from about 5 to about 100 mM, more preferably, 1 to 20 mM, and most preferably 25 to 75 mM.

In some embodiments, the buffer is combined with the salt of a divalent cation and the antibody or fragment thereof as a solid. In another embodiment of the invention, the buffer is combined with the divalent cation salt and the antibody as a solution. In a further embodiment of the invention, solid buffer and solid divalent salt can be put into solution and then combined with the antibody, either in solution or in a solid form.

Typically, the pH of the solution depends at least in part on the specific buffer that is used. In one embodiment, the desired pH of the solution depends at least in part on the salt of the divalent cation and solubility of the salt at different pHs. In some embodiments, the pH of the buffer may range from about 4.5 to about 9. In embodiments, where the divalent cation is Zn, the pH of the solution is between about 4 and 6. In another embodiment of the invention, where the divalent cation is Zn, the concentration of the sodium acetate in the solution is between about 1 and 100 mM, and the pH of the solution is between about 4.7 and 5.7. In other embodiments, the divalent cation is Mg, the buffer is Tris, and the pH of the solution is about 7.5 to 9.

In one embodiment, the pH of the solution, the buffer that is used, and the divalent salt that is used may depend at least in part on the antibody to be crystallized. In some embodiments of the invention, there may be an interplay between these factors because the antibody may be stable within a specific pH range, which could dictate, at least in part the buffer to be used, and similarly may dictate at least in part the divalent salt to be used (due to solubility issues for example). One of skill in the art can determine what buffer concentration and concentration of salt of the divalent cation by doing a solubility curve and identifying the ranges of concentration or buffer, divalent salt and pH that results in a phase change.

In some embodiments, antibody or fragments thereof, are crystallized with at least 25 mM zinc salt and at least 50 mM buffer, such as sodium acetate. In other embodiments, a combination of about 10 to 80 mM of zinc salt and about 25 to 75 mM buffer, such as sodium acetate, is preferable.

Methods of the invention comprise contacting the solution and the antibody or fragment thereof. In some embodiments, the antibody or fragment thereof is contacted with the solution in a vapor diffusion method. In vapor diffusion, a small volume (i.e. a few millimeters) of antibody, or fragment thereof, solution is mixed with the solution. This mixture is suspended over a well containing a small amount of solution. In other embodiments, the method of contacting involves dialysis. Dialysis involves a semi-permeable size exclusion membrane that retains the antibody or fragment thereof, but allows small molecules such as buffers and precipitants to diffuse in and out. The precipitant slowly diffuses through the membrane and reduces the solubility of the antibody or fragment thereof. Another embodiment is a batch type method. In the batch method, the solution is added to the solution of the antibody or fragment thereof.

The methods of the invention comprise incubating the antibody or fragment thereof with the solution until crystals or a protein gel are formed. In some embodiments, the solution may be gently mixed once or twice per day during the incubation. In other embodiments, the solution may be mixed continuously. If large crystals are desired mixing should be minimized.

Incubation can be conducted over a range of temperatures from about 0° C. to about 27° C., more preferably about 2 to 25° C. In some embodiments, the temperature is maintained at ambient temperature (e.g. about 25° C.). In other cases, incubation is conducted at from about 2 to 8° C.

A solution and antibody, or fragment thereof, are incubated until crystals or protein gel are formed. Typically, the time of incubation is from about 1 hour to 30 days, more preferably 1 to 5 days.

Crystals may be formed as free solids or in a gel. In some embodiments of the invention, the crystals of antibodies or fragments thereof are part of a gel. Generally, gels formed in methods of the invention have a high concentration of antibody or antibody fragments. In one embodiment, a gel that is formed using a method of the invention has a concentration of about 200 to about 250 mg antibody/mL.

Compositions or Formulations

Methods of the invention involve the formation of crystals or protein gels of antibodies, or fragments thereof. Crystals have a regular three-dimensional structure, typically refeffed to as a lattice. This is in contrast to an amorphous solid which is a non-crystalline solid that has no regular molecular lattice and has a heterogeneous or no molecular structure. A gel is a concentrated protein solution that can be soft and viscous or hard and brittle.

Crystals formed in the methods described herein can have a variety of shapes including needles, cone-like shapes; spherical and flower-like. The size of the crystals can be on the order of mm to μm size. In some embodiments, the crystals are at least about 10 μm in size, so that they are visible to the naked eye. For therapeutic administration, the size of the crystals will vary depending on the route of administration, for example, for subcutaneous administration the size of the crystals may be larger than for intravenous administration.

In some cases, it may be desirable to verify that the crystals are crystals of antibody, or fragment thereof. Crystals of antibody fragments thereof can be analyzed microscopically under birefringent light. Crystals will allow birefringent light to pass through, whereas non-crystalline material does not. In yet another method, crystals can be isolated, washed, resolubilized and run on SDS-PAGE gel and, optionally, stained with an anti-Fc receptor antibody. Optionally, the resolubilized antibody, or fragment thereof, can also be tested for binding to its 10 specific antigen utilizing standard assays. The resolubilized antibody or fragment thereof can also be analyzed by mass spectrometry.

In some cases, crystals can be crosslinked to one another. Such crosslinking may enhance stability of the crystal. Methods for crosslinking crystals are known to those of skill in the art and have been described, for example, in U.S. Pat. No. 5,849,296. Crystals can be crosslinked using a bifunctional reagent such as glutaraldehyde. Once crosslinked, crystals can be lyophilized and stored for use, for example, in diagnostic or therapeutic applications.

In some cases, it may be desirable to dry the crystals or protein gels. Crystals or protein gels may be dried with $N_2$, and/or inert gases, vacuum oven drying, lyophilization, evaporation, tray drying, fluid bed drying, spray drying, vacuum drying or roller drying.

Crystals can be maintained in the solution, or they can be washed and combined with other carriers and/or ingredients to form compositions and/or formulations of the crystals. The compositions and formulations can be used, for example, in therapeutic and diagnostic applications.

Another aspect of the invention involves compositions and/or formulation of crystals or protein gels of the antibody or fragment thereof. A composition comprises a crystal or protein gel of an antibody, or fragment thereof, and a carrier. A formulation comprises a crystal or protein gel of an antibody, or fragment thereof, and at least one ingredient. In some embodiments, the antibody is selected from the group consisting of anti-VEGF, anti-Apo-2, anti-CD20, anti-CD11a, anti-HER2, anti-IgE, and fragments thereof.

Formulations or compositions of the crystal or protein gel of the antibody or antigen binding fragment are prepared for storage by mixing the antibody having the desired degree of purity with physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or iminoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; and/or non-ionic surfactants such as TWEEN™, PLURONICS™ or polyethylene glycol (PEG).

In some embodiments, the crystals or protein gels may be combined with a polymeric carrier to provide for stability and sustained release. Such polymers include biocompatible and biodegradable polymers. A polymeric carrier may be a single polymer type or it may be composed of a mixture of polymer types. Nonlimiting examples of polymeric carriers include, for example, poly(acrylic acid), poly(cyanoacrylates), poly(amino acids), poly(anhydrides), poly(depsipeptide), poly(esters) such as poly(lactic acid) or PLA, poly(lactic-co-glycolic acid) or PLGA, poly(β-hydroxybutryate), poly(caprolactone) and poly(dioxanone); poly(ethylene glycol), poly((hydroxypropl)methacrylamide, poly[(organo)phosphazene], poly(ortho esters), poly(vinyl alcohol), poly(vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, modified starches such as amylose starch, amylopectin starch, hydroxyethyl starch, methacrylate starch, and other starches, and any conventional material that will encapsulate protein crystals.

Formulations of crystals of antibodies, or fragments thereof, include at least one ingredient or excipient. Ingredient or excipients are known to those of skill in the art and include acidifying agents, aerosol propellants, alcohol denaturants, alkalizing agents, anticaking agents, antifoaming agents, microbial preservatives, anti-antioxidants, buffering agents, lubricants, colors, dessicants, emulsifying agents, filtering aids, flavors and perfumes, humectants, ointments, plasticizers, solvents (e.g. oils or organic), sorbents, carbon dioxide sorbents, stiffening agents, suppository bases, suspending or viscosity increasing agents, sweetening agents, tablet binders, table or capsule diluents, tablet disintegrants, tablet or capsule lubricants, tonicity agent, flavored or sweetened vehicles, oleaginous vehicles, solid carrier vehicles, water repelling agent, and wetting or solubilizing agents.

In some embodiments, the ingredient enhances storage stability. In other embodiments, the ingredient or excipient is preferably selected from the group consisting of albumin, sucrose, trehalose, lactitol, gelatin, and hydroxyproyl-β-cyclodextrin.

Compositions and formulations described herein also comprise an effective amount of crystalline antibody or fragment thereof. Dosages can readily be determined using standard methodology. The antibody is suitably administered to the patient at one time or over a series of treatments.

Depending on the type and severity of the disease, about 1 μg/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 μg/kg to about 20 mg/kg or more, depending on the condition, the treatment is repeated until a desired suppression of disease symptoms occurs. However, other dosage regimens may be useful.

In some cases, compositions or formulations comprise a concentration of antibody, or fragment thereof, at least about 1 g/L or greater when resolubilized. In other embodiments, the antibody concentration is at least about 1 g/L to about 100 g/L when resolubilized.

Crystals and/or protein gels of an antibody or antibody fragment thereof, or formulations or compositions comprising such crystals or protein gels, may be administered alone, as part of a pharmaceutical, personal care or veterinary preparation, or as part of a prophylactic preparation, with or without adjuvant. They may be administered by parenteral, oral or topical routes. For example, they may be administered by oral, pulmonary, nasal, aural, anal, dermal, ocular, intravenous, intramuscular, intraarterial, intraperitoneal, mucosal, sublingual, subcutaneous, transdermal, topical or intracranial routes, or into the buccal cavity. In either pharmaceutical, personal care or veterinary applications, crystals of antibodies, or fragments thereof, or crystal formulations or compositions thereof may be topically administered to any epithelial surface. Such epithelial surfaces include oral, ocular, aural, anal and nasal surfaces, which may be treated, protected, repaired or detoxified by application of crystals of an antibody or fragment thereof, or crystal formulations or compositions thereof.

Another aspect of the invention includes articles of manufacture. Articles of manufacture comprise a composition or formulation comprising a crystal or protein gel of antibody or fragment thereof and a container. The antibodies or fragments thereof are preferably anti-VEGF, anti-CD20, anti-Apo-2, anti-CD11a, anti-HER2, anti-IgE, or fragments thereof. Optionally, the article of manufacture may include instructions for administration to a human for therapeutic use.

Articles of manufacture can also comprise a composition or formulation of a crystal or protein gel of an antibody, or fragments thereof, and a variety of diagnostic reagents for detecting the binding antibody, or fragment thereof, to its specific antigen. Agents for detecting the binding of the antibody to its specific antigen include antibodies to the antibody that are labeled with a detectable agent. The detectable agent can include a fluorescent moiety, radioactive moiety, and an enzymatic moiety. In some embodiments, an article of manufacture comprises a composition or a formulation of a crystal or protein gel of an antibody or fragment thereof and a container. The article of manufacture may further comprise instructions for administering the composition or formulation to a human. In other embodiments, the article of manufacture further comprise an agent for detecting the binding of the antibody or fragment to its specific antigen.

Uses of Compositions or Formulations

The compositions or formulations of the inventions comprising crystals or protein gel of antibody, or fragments thereof, can be used for any purpose that conventional antibody preparations are used for. For example, compositions or formulations may be utilized, for example, for purification, concentration, imaging, diagnostic and/or therapeutic applications. In some embodiments, protein gels or crystals that are present in gels can be used for topical administration, as a solution from which further crystallization or purification takes place, or as a solution for storage of the crystals.

In some embodiments, the compositions or formulations comprise a crystal of, crystalline, or protein gel of anti-VEGF antibody, or fragment thereof. These compositions or formulations are useful in diagnostic methods and methods of treating VEGF associated disorders or conditions. VEGF associated disorders or conditions and diagnostic assays have been described, for example, in WO 98/45331. The anti-VEGF antibodies are useful in the treatment of various neoplastic and non-neoplastic diseases and disorders. Neoplasms and related conditions that are amenable to treatment include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

Non-neoplastic conditions that are amenable to treatment include rheumatoid arthritis, psoriasis, atherosclerosis, diabetic and other proliferative retinopathies including retinopathy of prematurity, retrolental fibroplasias, neovascular glaucoma, age-related macular degeneration, thyroid hyperplasias (including Grave's disease), corneal and other tissue transplantation, chronic inflammation, lung inflammation, nephritic syndrome, preeclampsia, ascites, pericardial effusion (such as that associated with pericarditis), and pleural effusion.

Agent-related macular degeneration (AMD) is a leading cause of severe visual loss in the elderly population. The exudative form of AMD is characterized by choroidal neovascularization and retinal pigment epithelial cell detachment. Because choroidal neovascularization is associated with a dramatic worsening in prognosis, the VEGF antibodies of the present invention are expected to be especially useful in reducing the severity of AMD.

In some embodiments, the compositions or formulations of the invention comprise a crystal, crystalline, or protein gel of anti-CD11a. These compositions or formulations are useful in diagnostic methods and methods of treating CD11a associated disorders or conditions. CD11a associated disorders or conditions and diagnostic assays are described in U.S. Pat. No. 6,037,454, which is hereby incorporated by reference.

The anti-CD11a (the α-subunit of LFA-1) antibody may be used to treat various LFA-1 mediated disorders. Lymphocyte function-associated antigen 1 (LFA-1; CD11a/CD18) is involved in leukocyte adhesion during cellular interactions essential for immunologic responses and inflammation. The term "LFA-1-mediated disorder" refers to a pathological state caused by cell adherence interactions involving the LFA-1 receptor on lymphocytes. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitis; allergic conditions such as eczema and asthma; conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; chronic obstructive pulmonary disease (COPD); bronchitis; insulinitis; rhinitis; urticaria; glomerulonephritis; diseases involving leukocyte diapedesis; CNS inflammatory disorder; multiple organ injury syndrome secondary to septicaemia or trauma; autoimmune hemolytic anemia; myethemia gravis; antigen-antibody complex mediated diseases; nephrotic syndrome; malignancies (e.g., B-cell malignancies such as chronic lymphocytic leukemia or hairy cell leukemia); all types of transplantations, including graft vs. host or host vs. graft disease; HIV and rhinovirus infection; pulmonary fibrosis; invasion of tumor cells into secondary organs etc.

In some embodiments, the compositions or formulations of the invention comprise a crystal, crystalline, or protein gel of anti-HER2. These compositions or formulations are useful in diagnostic methods and methods of treating HER2 associated disorders or conditions. HER2 associated disorders or conditions and diagnostic assays are described in U.S. Pat. No. 6,387,371, which is hereby incorporated by reference.

Adminstration to a patient of a therapeutically effective amount of anti-HER2 receptor antibodies inhibit tumor cell growth by inhibiting the HER2 receptor function. Trastuzumab (Genentech, Inc.) is a recombinant humanized monoclonal antibody directed at the HER2 extracellular domain for the treatment of HER2 over-expressed/HER2 gene amplified cancer, particularly metastatic breast cancer (MBC). The HER2 gene can also amplified be in salivary gland adenocarcinoma, renal adenocarcinoma, mammary gland carcinoma, and gastric cancer cell line. The antibody can also be administered to patients in combination with other therapeutics, e.g., paclitaxel or Tarceva®.

In some embodiments, the compositions or formulations of the invention comprise a crystal, crystalline, or protein gel of anti-CD20. These compositions or formulations are useful in diagnostic methods and methods of treating CD20 associated disorders or conditions. CD20 associated disorders or conditions and diagnostic assays are described in U.S. Pat. Nos. 6,171,586 and 5,736,137, which are hereby incorporated by reference. CD20 (also known as Bp35) is an antigen of interest for targeting disease relating to B-cell neoplasms due to its expression at very high levels. CD20 is a human B cell marker that is expressed during early pre-B cell development and remains until plasma cell differentiation. The CD20 molecule may regulate a step in the activation process that is required for cell cycle initiation and differentiation. Thus, the CD20 surface antigen can be targeted for treating B-cell lymphoma.

C2B8 is a specific immunologically active, chimeric anti-CD20 antibody. Therapeutic intervention with the C2B8 antibody purges or depletes B cells in peripheral blood and lymphatic tissue as a means of removing B cell lymphomas since mammalian systems readily and efficiently recover peripheral blood B cells. When the immune system has a peripheral blood B cell deficiency, the need for "extraordinary" precautions (i.e. patient isolation, etc.) is not necessary since the principal immune response of primates is T-cell mediated. C2B8 can also be tagged with radioactive labels to destroy target tumor cells.

In some embodiments, the compositions or formulations of the invention comprise a crystal, crystalline, or protein gel of anti-Apo-2 antibody. These compositions or formulations are useful in treating disorders, such as cancer. The therapeutic uses for an anti-Apo-2 antibody are described in U.S. Pat. No. 6,252,050, which is hereby incorporated by reference. Accordingly, the invention provides methods for treating cancer using antibodies, such as cross-reactive Apo-2L receptor antibodies. Agonistic Apo-2 antibodies, for instance, may be employed to activate or stimulate apoptosis in cancer cells. It is of course contemplated that the methods of the invention can be employed in combination with still other therapeutic techniques such as surgery.

In some embodiments, compositions or formulations of the invention comprise a crystal, srystalline, or proten gel of an anti-IgE antibody. (These compositions or formulations are useful in treating IgE meditated disorders, for example allergic disorders and inflamation.) The therapeutic uses for an anit-IgE antibody are described in U.S. Pat. Nos. 6,329,509 and 5,994,511, which are hereby incorporated by reference.

Antibodies and labeled antibodies may be used in a variety of immunoimaging or immunoassay procedures to detect the presence of cancer in a patient or monitor the status of such cancer in a patient already diagnosed to have it. When used to monitor the status of a cancer, a quantitative immunoassay procedure must be used. If such monitoring assays are carried out periodically and the results compared, a determination may be made regarding whether the patient's tumor burden has increased or decreased. Common assay techniques that may be used include direct and indirect assays. If the sample includes cancer cells, the labeled antibody will bind to those cells. After washing the tissue or cells to remove unbound labeled antibody, the tissue sample is read for the presence of labeled immune complexes. In indirect assays the tissue or cell sample is incubated with unlabeled monoclonal antibody. The sample is then treated with a labeled antibody against the monoclonal antibody (e.g., a labeled antimurine antibody), washed, and read for the presence of ternary complexes.

Although the foregoing refers to particular embodiments, it will be understood that the present invention is not so limited. It will occur to those of ordinary skill in the art that various modifications may be made to the disclosed embodiments without changing from the overall concept of the invention. All such modifications are intended to be within the scope of the invention. All references cited throughout the specification are hereby expressly incorporated by reference.

EXAMPLE 1

Solubility of Anti-VEGF Antibody in Various Concentrations of Zinc Chloride and Sodium Acetate Crystallization of full length and/or glycosylated antibodies can be difficult. The size, shape and presence of sugar moieties contribute to the difficulty of obtaining crystals of antibody. Many different combinations of organic and non-organic precipitants, buffers, and cosolutes may need to be investigated to find the conditions suitable for crystallization of antibodies. The solubility of a full length glycosylated antibody of VEGF in solutions of varying concentrations of $ZnCl_2$ and NaOAc was investigated to determine whether antibody protein crystals could be formed with these conditions.

Materials and Methods

Preparation and Purification of Anti-VEGF Antibody

Anti-VEGF antibody, (bevacizumab) can be prepared generally as described in WO 98/45331 and Presta et al., *Can. Res.*, 57:4593-4599, the disclosure of which are incorporated herein by reference. The process is also generally described below.

A murine antibody specific for VEGF, designated A4.6.1 (Kunkel et al., 1985, *Proc. Natl. Acad. Sci. USA,* 82:488-492) was cloned and sequenced. A synthetic consensus sequence for human light and heavy chain variable domains was used to generate a computer graphics model into which the murine CDRs could be imported using the program Insight™ (Accelrys, Inc. San Diego Calif.). Computer models of the $V_H$ and $V_L$ regions of the murine antibody A4.5.1 were also generated to determine confirmation of the CDRs.

Plasmids encoding all F(ab) humanized variants of A4.6.1 were constructed from the plasmid template for F(ab)-1. Plasmid pEMX1 (Kunkel et al., 1985 *Proc. Natl. Acad. Sci. USA,* 82:488-492) contains a DNA fragment encoding consensus human $V_L$P subgroup I and $V_H$ subgroup III. The humanized anti-VEGF was constructed by site directed mutagenesis of pEMX1 (Kunkel et al., 1985 *Proc. Natl. Acad. Sci. USA,* 82:488-492). Nucleic acid sequences encoding anti-VEGF antibodies are provided in WO 98/45331.

One example of a method of producing anti-VEGF is described herein. For expression of stable humanized IgG1 variant (rhuMAb VEGF), Chinese hamster ovary (CHO) cells were transfected with dicistronic vectors designed to coexpress both heavy and light chains (Lucas et al., 1996 *Nucleic Acids Res.,* 24:1774-1779). Plasmids were introduced into DP12 cells, a proprietary derivative of the CHO-K1 DUX B11 cell line developed by L. Chasin (Columbia University, New York, N.Y.), via lipofectin and were selected for growth in glycine/hypoxanthine/thymidine (GHT)-free medium (Chisolm et al., 1996 DNA Cloning 4. Mammalian systems, pp. 1-41, Oxford: Oxford University Press).

Twenty unamplified clones were randomly chosen and reseeded into 96 well plates. Relative specific productivity of each colony was monitored using ELISA to quantitate the full-length human IgG accumulated in each well after three days. A fluorescent dye, Calcein AM, was used as a surrogate marker of viable cell number per well. Based on these data, several unamplified clones were chosen for further amplification in the presence of increasing concentrations of methotrexate. Individual clones surviving at 10, 50, and 100 nM methotrexate were chosen and transferred to 96 well plates for productivity screening.

One clone, which reproducibly exhibited high specific productivity, was expanded in T-flasks and used to inoculate a spinner culture. After several passages, the suspension-adapted cells were used to innoculate production cultures in GHT-containing, serum-free media supplemented with various hormones and protein hydrolysates. Harvested cell culture fluid containing rhuMAb (recombinant humanized monoclonal antibody) VEGF was purified using protein A-Sepharose® CL-4B. The purity after this step was ~99%. Subsequent purification to homogeneity was carried out using an ion exchange chromatography step utilizing Q Sepharose® followed by CM Sepharose®. The endotoxin content of the final purified antibody was <0.10 eu/mg. The purified antibody was concentrated and further purified using ultrafiltration and diafiltration. Alternative methods for purification and/or concenration include tangential flow filtration.

Crystallization Conditions

Anti-VEGF prepared as described above was dialyzed into Milli-Q® water and concentrated to 84.4 g/L. The pH of a 1M NaOAc stock solution was adjusted to pH 5.7 with 6N HCl. The buffers were prepared following a serial dilution scheme and the pH was adjusted to pH 5.7 with 1N NaOH. The concentrations of $ZnCl_2$ ranged from 5 to 100 mM and the NaOAc concentration varied from 10 to 100 mM.

The dialysis method of crystallization utilized a semi-permeable size-exclusion membrane that retains protein but allows small molecules (i.e. buffers and precipitants) to diffuse freely through the membrane. The dialysis method included using one (1) mL of the anti-VEGF stock solution injected into a Slide-a-Lyzer® dialysis cassette (Pierce, Rockford, Ill.) and dialyzed into each stock solution overnight at 5° C. The dialysis buffers were exchanged a total of three times over a three day period. The dialysis devices were continually mixed in each stock solution and the resulting material was recovered after three days. The material was recovered by carefully slicing the dialysis cassette membrane and transferring the gel solution into a tube using a sterile spatula. Solubility curves were generated by measuring the protein concentration of the material recovered from the dialysis cassette. The protein concentration was plotted against the concentration of $ZnCl_2$.

Results

The solubility curve of anti-VEGF in $ZnCl_2$ and NaOAc, pH 5.7 is shown in FIG. 1.

As the $ZnCl_2$ concentration increases, a decrease in the solubility of anti-VEGF is observed. During dialysis of the anti-VEGF into varying concentrations of $ZnCl_2$ in a NaOAc buffer, the formation of gels was observed in the dialysis cassettes. The gel initially started out cloudy. The gel with crystals formed within 25 minutes of dialysis from buffers containing as low as 2 mM $ZnCl_2$ at room temperature and at 4° C. The gels were further analyzed by microscopy and crystalline material was observed in the gels. The crystals within the gel were very small and uniform. When observed under a microscope, the crystals within the gel displayed birefringence when viewed under cross polarizers indicating that it was crystalline material.

Many conditions including organic and inorganic precipitants with a variety of buffers and cosolutes were previously investigated for the ability to crystallize a full-length glycosylated antibody. Many of the conditions investigated did not result in the formation of crystals of the antibody (data not shown). It was desirable to design a crystallization process that avoids the use of organic precipitants, especially for antibodies that are to be used therapeutically.

Our studies indicated that a combination of a divalent cation such as in the form of a salt such as $ZnCl_2$ in a NaOAc buffer could be utilized to form crystals of full-length antibodies without any organic precipitant. The solubility of anti-VEGF antibody in varying concentrations of $ZnCl_2$ in a NaOAc buffer allows a determination of the concentration of $ZnCl_2$ in NaOAc in which anti-VEGF becomes insoluble resulting in the formation of crystals. At low concentrations of $ZnCl_2$, free crystals are observed. Increasing $ZnCl_2$ concentrations results in the formation of a gel containing crystals. The results of the solubility study determined the concentration range used for the batch crystallization study in the next example.

EXAMPLE 2

Crystallization of Anti-VEGF with Zinc Chloride and Sodium Acetate

As described in Example 1, anti-VEGF solutions dialyzed with solutions of varying concentrations of $ZnCl_2$ and NaOAc became insoluble at certain concentrations and resulted in the formation of crystals and/or gels. Crystallization of anti-VEGF with solutions of $ZnCl_2$ and NaOAc without organic precipitants was studied under both dialysis conditions and batch conditions. The crystals obtained were further characterized. Crystallization under batch conditions is desirable because these conditions can be scaled up to large-scale production.

Material and Methods
Crystallization Methods and Analysis

Anti-VEGF was prepared by concentrating anti-VEGF from 36 g/L to 84.4 g/L by centrifugal ultrafiltration and dialyzed into Milli-Q® water. The resulting concentration of anti-VEGF was 84.4 g/L and was incubated with varying concentrations of $ZnCl_2$ and NaOAc either by dialysis or in batch. The anti-VEGF concentration was determined by measuring absorbance at 280 nm.

Four crystallization stock solutions of $ZnCl_2$ and NaOAc were also made as follows:
  1: 10 mM $ZnCl_2$, 100 mM NaOAc, pH 5.7
  2: 50 mM $ZnCl_2$, 100 mM NaOAc, pH 5.7
  3: 50 mM $ZnCl_2$, 10 mM NaOAc, pH 5.7
  4: 50 mM $ZnCl_2$, pH adjusted to 5.7 with sodium hydroxide
The combinations of concentration of $ZnCl_2$ and NaOAc are shown in Table 1a.

The dialysis method was carried out using one (1) mL of the anti-VEGF stock solution placed in a Slide-a-lyzer® dialysis device (Pierce, Rockford, Ill.) and dialyzed into each stock solution. The dialysis devices were continually mixed in each stock solution and the resulting material was scraped out of the device and placed in an eppendorf tube after five days.

The experiment was also carried out using a "batch" method. The batch method started by adding 0.75 mL of the anti-VEGF stock solution in a 1:1 ratio (i.e. 0.75 mL) with each of the crystallization stock solutions in eppendorf tubes.

Each tube was tipped over twice per day to provide gentle mixing. The tubes were held at ambient temperature and tipped twice for five days.

TABLE 1a

| Condition # | ZnCl$_2$ (mM) | NaOAc pH 5.7 (mM) | Method | anti-VEGF (g/L) | scale (mL) |
|---|---|---|---|---|---|
| 1 | 10 | 100 | dialysis | 84.4 | 1 |
| 2 | 50 | 100 | dialysis | 84.4 | 1 |
| 3 | 50 | 10 | dialysis | 84.4 | 1 |
| 4 | 50 | 0 | dialysis | 84.4 | 1 |
| 5 | 5 | 50 | batch | 42.2 | 1.5 |
| 6 | 25 | 50 | batch | 42.2 | 1.5 |
| 7 | 25 | 5 | batch | 42.2 | 1.5 |
| 8 | 25 | 0 | batch | 42.2 | 1.5 |

Microscopic Analysis of Crystals

After the material was recovered, the crystals were analyzed microscopically for morphology in the presence or absence of birefringent light. The use of birefringent light distinguishes between crystalline solids and solid precipitate. The analysis was accomplished by passing light between two polarizing filters. One filter was placed below the sample and the other filter was placed above the sample. If the sample is not crystalline, the two polarizing filters will block the light from reaching the observer. If the sample is crystalline, it will bend the light allowing it to pass through the second filter and into the observer's eye. Crystals were analyzed microscopically by placing a sample on a slide and viewing the crystals at various magnifications.

Other methods were used to test the solid material including staining with Izit dye and crush/crack test. The crush/crack test was inconclusive because most or the crystalline material was too small to allow a determination of crush vs. crack. Izit dye results were also not consistent as many false negatives and false positives were observed.

Results

The results are shown in Tables 1b and 1c.

Table 1b shows the visual observations made at day 1, 2, and 5 of the samples under the various conditions, as given in Table 1a.

TABLE 1b

| Condition # | Day 1 | Day 2 | Day 5 |
|---|---|---|---|
| 1 | opalescent | opalescent | chunky solids |
| 2 | liquid white | liquid white | chunky/gel solids |
| 3 | liquid white | liquid white | Gel |
| 4 | opalescent, white solids | opalescent, white solids | opalescent, white solids |
| 5 | some white solid | Clear | Clear |
| 6 | full of white solids | gel on bottom | Gel |
| 7 | clear solid | Clear | Clear |
| 8 | white solid | gel on bottom | gel on bottom |

Table 1c shows the analytical measurements that were carried out on the recovered material from the samples under the various conditions as given in Table 1a. The solids formed displayed birefringence when viewed under cross polarizers, but in most cases were too small for a regular shape, or morphology, to be recognized.

TABLE 1c

| Condition # | Birefringent | Crystal Morphology |
|---|---|---|
| 1 | Yes | No |
| 2 | Yes | No |
| 3 | Yes | No |
| 4 | No | No |
| 5 | Yes | Infrequent Cones |
| 6 | Yes | Flowers |
| 7 | Yes | Lots of Cones |
| 8 | No | No |

These results show that anti-VEGF was crystallized using combinations of ZnCl$_2$ and NaOAc in both dialysis and batch methods. Every condition studied caused anti-VEGF to change its phase immediately after it contacted the precipitant solution. Solids displaying birefringence were observed in every condition containing ZnCl$_2$ and NaOAc, indicating that crystals were formed in each of these conditions. In some cases, the crystals that were observed were inside a gel-like phase of anti-VEGF. In some cases, the crystals could not be isolated from the gel, so it could not be definitively shown that they were anti-VEGF crystals. The crystals form cone like or flower type structures. This example showed that anti-VEGF crystals can be produced by either dialysis or batch methods using ZnCl$_2$ and NaOAc without the use of organic precipitants.

Figure 2A:
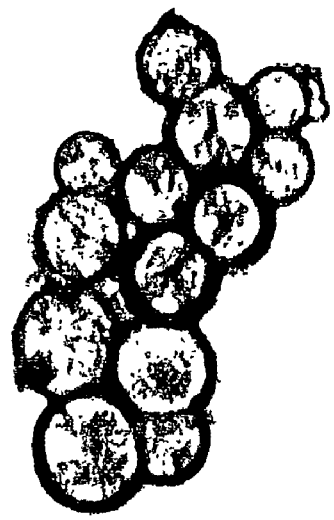
FIG. 2a is an image at 200× magnification of anti-VEGF crystals formed in the presence of 5 mM $ZnCl_2$ and 100 mM NaOAc, pH 5.7 under non-birefringent light.
Figure 2B:
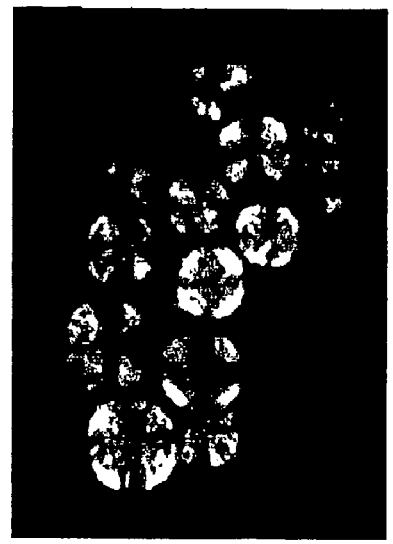
FIG. 2b is an image at 200× magnification of anti-VEGF crystals formed in the presence of 5 mM $ZnCl_2$ and 100 mM NaOAc, pH 5.7, under birefringent light.
Figure 2C:
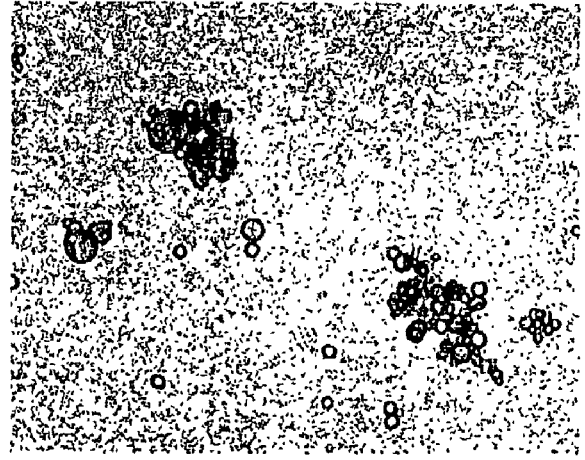
FIG. 2c is an image at 200× magnification of anti-VEGF crystals formed in the presence of 25 mM $ZnCl_2$ and 10 mM NaOAc, pH 5.7, under non-birefringent light.
Figure 2D:
FIG. 2d is an image at 200× magnification of anti-VEGF crystals formed in the presence of 25 mM $ZnCl_2$ and 10 mM NaOAc, pH 5.7, under birefringent light.
Figure 2E:
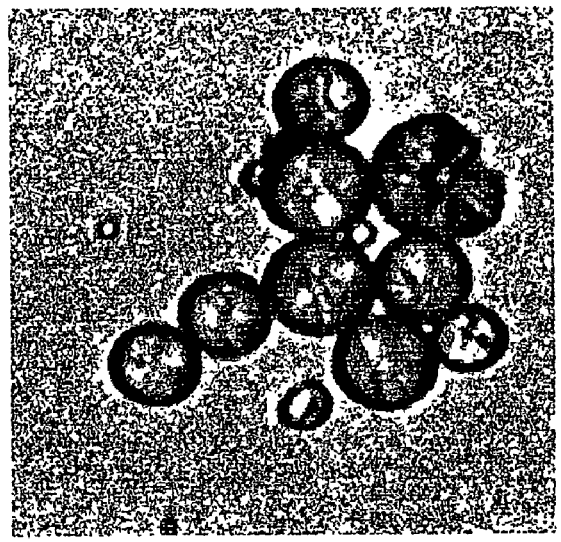
FIG. 2e is an image at 200× magnification of anti-VEGF crystals formed in a solution of 10 mM $ZnCl_2$, 100 mM NaOAc, pH 5.7, under non-birefringent light.
Figure 2F:
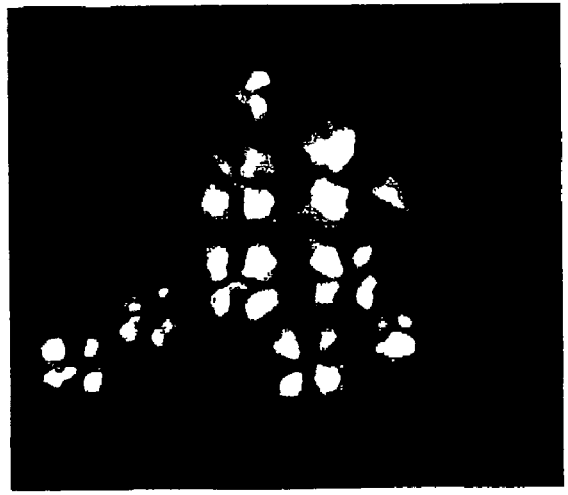
FIG. 2f is an image at 200× magnification of anti-VEGF crystals formed in a solution of 10 mM $ZnCl_2$, 100 mM NaOAc, pH 5.7, under birefringent light.

Representative images under birefringent and non-birefringent light are shown in FIGS. 2a-2f. FIG. 2a is an image at 200× magnification of anti-VEGF crystals formed in the presence of 5 mM ZnCl$_2$ and 100 mM NaOAc, pH 5.7 under non-birefringent light. FIG. 2b is an image at 200× magnification of anti-VEGF crystals formed in the presence of 5 mM ZnCl$_2$ and 100 mM NaOAc, pH 5.7, under birefringent light. FIG. 2c is an image at 200× magnification of anti-VEGF crystals formed in the presence of 25 mM ZnCl$_2$ and 10 mM NaOAc, pH 5.7, under non-birefringent light. FIG. 2d is an image at 200× magnification of anti-VEGF crystals formed in the presence of 25 mM ZnCl$_2$ and 10 mM NaOAc, pH 5.7, under birefringent light. FIG. 2e is an image at 200× magnification of anti-VEGF crystals formed in a solution of 10 mM ZnCl$_2$, 100 mM NaOAc, pH 5.7, under non-birefringent light. FIG. 2f is an image at 200× magnification of anti-VEGF crystals formed in a solution of 10 mM ZnCl$_2$, 100 mM NaOAc, pH 5.7, under birefringent light.

EXAMPLE 3

Varying Crystallization Conditions

As described previously, anti-VEGF antibody was crystallized in a variety of concentrations of ZnCl$_2$ and NaOAc. Other crystallization conditions may affect the ability to crystallize the anti-VEGF or the yield of anti-VEGF crystals. The effect of changing pH, temperature and the identity of the divalent cation on the crystallization of anti-VEGF was examined.

Material and Methods

The stock solution of anti-VEGF at 87 g/L in Milli-Q® water was prepared by ultrafiltration and diafiltration on a 10 kD regenerated cellulose membrane. Each sample was comprised of a 1:1 ratio of protein to buffer solution, resulting in a final anti-VEGF concentration of 43.5 g/L. Stock solutions of 1M ZnCl$_2$, calcium chloride (CaCl$_2$), MgCl$_2$, were prepared by dissolving the appropriate amount of solids in Milli-Q water and filtering the solutions with a sterilizing grade filter. 1 molar stock solutions of NaOAc, pH 4.7, and NaOAc, pH 5.7 were prepared by adding the appropriate amount of sodium acetate trihydrate and glacial acetic acid to Milli-Q® water and filtered through a sterilizing grade filter.

The solution conditions were prepared by adding the appropriate amount of water, divalent ion stock solution, buffer stock solution, and protein stock solution. The protein stock solution was always added last.

Combinations of concentrations of $ZnCl_2$, $MgCl_2$, $CaCl_2$ and NaOAc were examined at two different pHs and temperatures. The concentrations of $ZnCl_2$ ranged from 5 to 100 mM and NaOAc ranged from 10 to 100 mM. The concentration of $MgCl_2$ ranged from 5 to 100 mM in NaOAc of 10 mM. The concentration of $CaCl_2$ ranged from 5 to 100 mM in NaOAc of 10 mM.

Crystallization using the batch method was conducted as described in Example 2, except each batch had a sample volume of 1 ml.

Results

The results are shown in Table 2. Combinations of $ZnCl_2$ and NaOAc were effective to form crystals and/or gels with crystals of full-length anti-VEGF antibody. The solid material was positive for crystalline material as determined by refraction of birefringent light. The anti-VEGF concentration in the supernatant was determined by measuring absorbance at 280 nm.

TABLE 2

| $ZnCl_2$ (mM) | NaOAc (mM) | pH | Temperature (°C.) | Observations | anti-VEGF conc. (g/L) | Birefringent Crystals |
|---|---|---|---|---|---|---|
| 5 | 10 | 4.7 | 4 | film | 43 | yes |
| 10 | 10 | 4.7 | 4 | film | 44 | yes |
| 100 | 10 | 4.7 | 4 | 20% gel | 16 | yes |
| 5 | 10 | 4.7 | Room | Film + solids | 44 | yes |
| 10 | 10 | 4.7 | Room | Lots of solids | 43 | yes |
| 100 | 10 | 4.7 | room | 17% gel | 18 | yes |
| 5 | 10 | 5.7 | 4 | Film + solids | 44 | yes |
| 10 | 10 | 5.7 | 4 | Film + solids | 42 | yes |
| 100 | 10 | 5.7 | 4 | 20% gel | 4.3 | yes |
| 5 | 10 | 5.7 | room | Film | 43 | yes |
| 10 | 10 | 5.7 | room | film and cloudy | 47 | yes |
| 100 | 10 | 5.7 | room | 17% gel | 3.8 | yes |

All of the $ZnCl_2$/NaOAc combinations produced crystals of anti-VEGF in gel or free in solution. Magnesium chloride and sodium acetate solutions did not show any effect on anti-VEGF under these conditions (data not shown). A calcium chloride and sodium acetate solution produced crystals with anti-VEGF when $CaCl_2$ was 100 mM and 10 mM NaOAc at pH 4.7 and incubated at 4° C. (data not shown).

Figure 5:
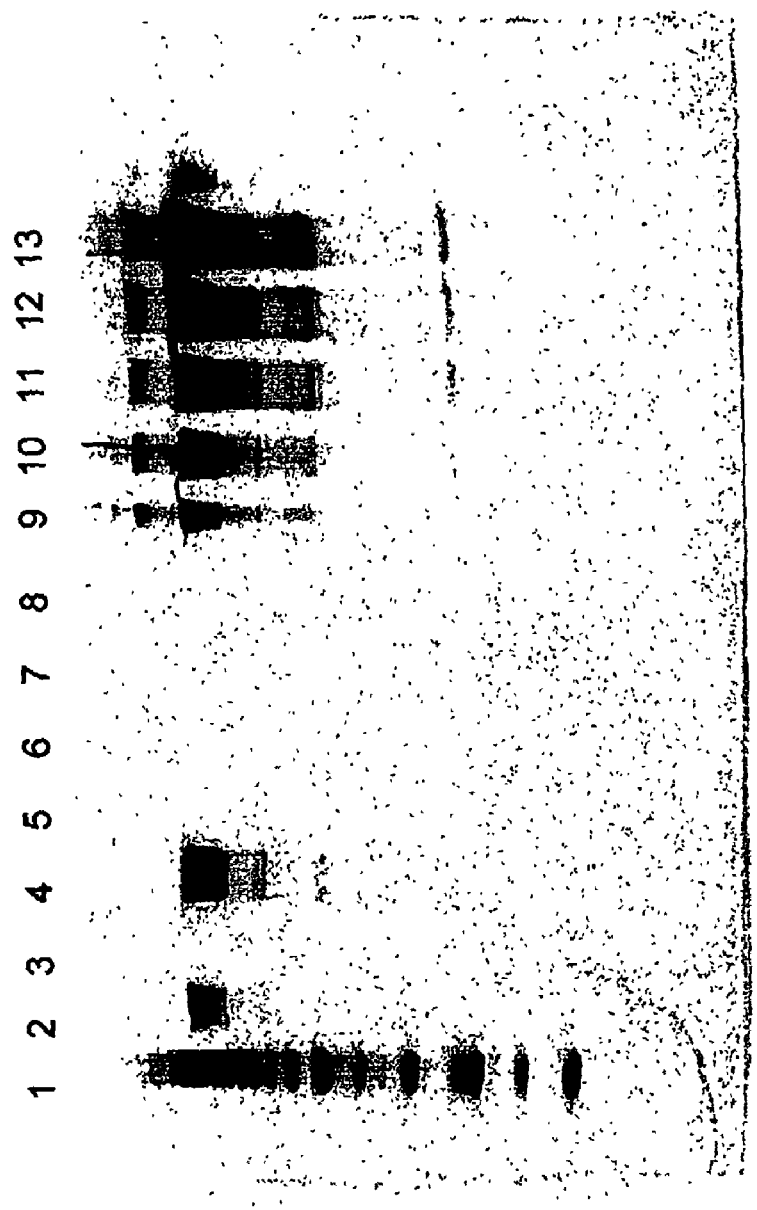
FIG. 5 shows a SDS-PAGE of anti-VEGF crystals that were isolated, washed, and resolubilized. Lane 1 is the molecular weight markers; Lane 2 is 5 μg of anti-VEGF; Lane 3 is empty; Lane 4 is the supernatant; Lane 5 is wash 1, mother liquor; Lane 6 is wash 2, mother liquor; Lane 7 is wash 3, mother liquor; Lane 8 is empty; Lane 9 is 1 ml crystal (dissolved in water); Lane 10 is 5 ml crystal (dissolved in water); Lane 11 is 10 ml of crystal (dissolved in water); Lane 12 is 15 ml crystal (dissolved in water); Lane 13 is 20 ml of crystal (dissolved in water).

The crystalline material was isolated from the solution formed with 100 mM $ZnCl_2$, and 10 mM NaOAC at pH 5.7, incubated at room temperature. The crystals were washed three times with 20 mM NaOAc and 20 mM $ZnCl_2$, pH 5.7 and the crystals were dissolved in water. Different amounts of resolublized crystals in water were run on SDS PAGE and compared to anti-VEGF before crystallization. The washes of the crystals were also tested for the presence of anti-VEGF. The results are shown in FIG. 5. The results show that the washes were negative for any anti-VEGF while resolublized crystals did have anti-VEGF. Increasing amounts of the crystals resulted in an increase in anti-VEGF detected.

The resolubilized anti-VEGF was also analyzed by mass spectroscopy and compared to control anti-VEGF. MALDI-TOF mass spectra of intact antibodies generally give a broad peak at 150 kDa and it is not easy to distinguish one antibody from other antibodies. However, the mass spectra from reduced antibodies exhibit high sensitivity for the light chain. As the light chain mass is unique to each antibody product, the samples were reduced with TCEP and analyzed in the linear positive mode. To account for concentration differences, the first two samples were diluted 50-fold and the next two samples were diluted 10-fold with sinapinic acid matrix solution and reduced with TCEP at room temperature (2 hr). Samples were spotted on the plate, air dried, washed with cold 0.1% TFA and mass spectra were acquired.

Figure 7A:
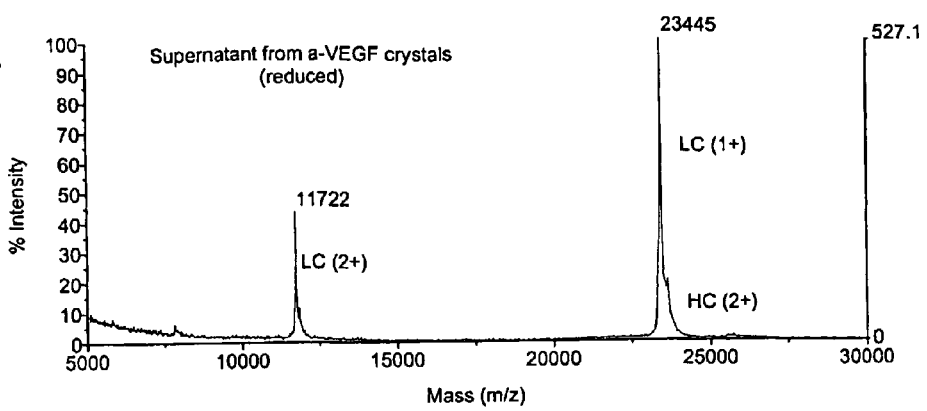
FIG. 7 shows mass spectroscopy analysis of anti-VEGF stock solution (D), anti-VEGF crystal solutions (A, C) and wash solution from crystals (B). The reduced ight chain of anti-VEGF has a mass of about 23,449 D.
Figure 7B:
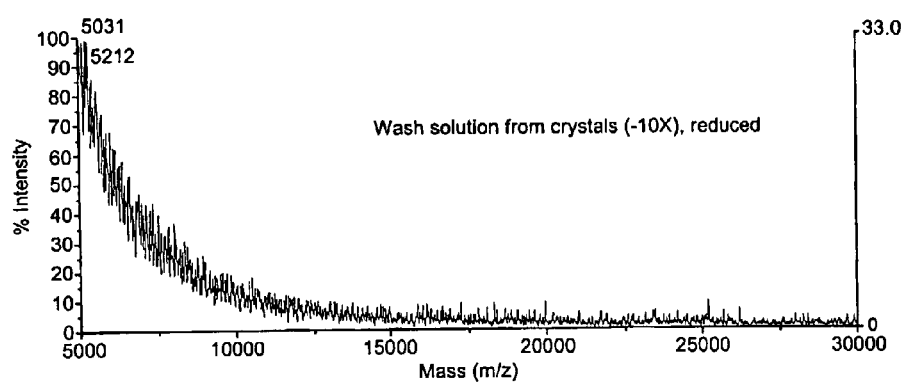
Figure 7C:
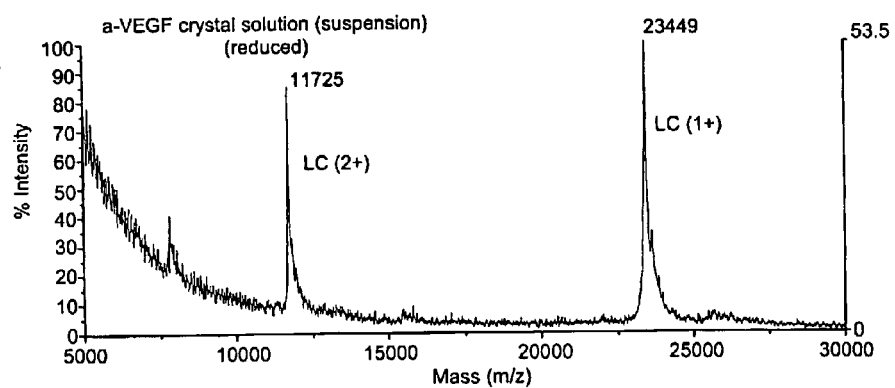
Figure 7D:
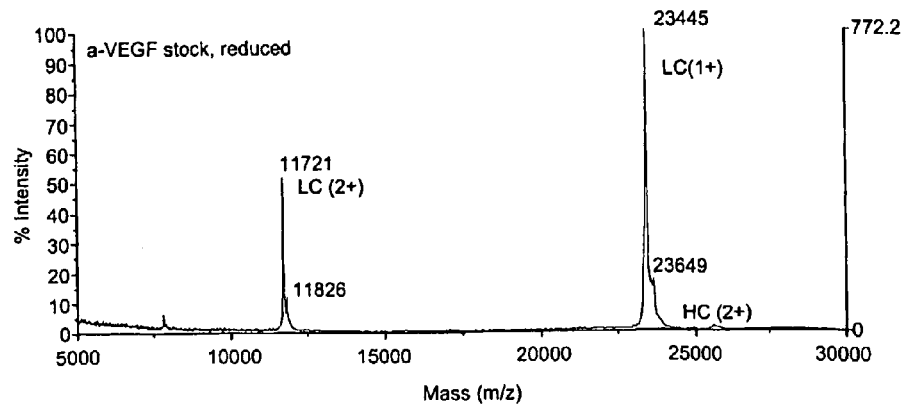

The molecular mass of anti-VEGF light chain is 23433 Da and MALDI-TOF mass spectra typically exhibit a mass accuracy of +/−0.05% in this mass range. The spectra of stock solution and supernatant exhibit similar patterns, that is a strong peak from singly and doubly protonated light chains and a weak doubly charged heavy chain. (FIGS. 7D, A, and C) The wash solution (under the conditions analyzed) did not show the presence of light chain (FIG. 7B), where as the crystal solution did show the light chain peaks.

Analysis of native Lys-C digest from the crystals by MALDI-TOFMS showed many anti-VEGF related peaks (as well as Lys-C autodigestion products). However, the digest from first wash solution also showed some of the anti-VEGF related peaks. (data not shown) One generally observes a higher sensitivity with the digests by MALDI-TOFMS compared to intact protein.

To summarize, anti-VEGF is clearly seen in the crystals, but first wash may also contain small amount of anti-VEGF. The results show that the resolubilized anti-VEGF from crystals had the same mass spectroscopy profile as control anti-VEGF.

EXAMPLE 4

Investigation of Gel-Liquid Phases of Anti-VEGF Solutions

Two phases have been identified in solutions containing anti-VEGF crystals. They include crystals free in solution and gels that may contain crystals. The anti-VEGF supernatant concentration directly relates to the crystal phase present. When gel is present, soluble anti-VEGF concentrations are typically less than about 10 g/L. When gel is not present, soluble anti-VEGF concentrations generally rise above 40 g/L.

Anti-VEGF's phase space of crystallization conditions was studied by varying NaOAc concentrations and $ZnCl_2$ concentrations at pH 5.7. By exploring the phase space, it may be possible to identify where the solution transitions from a gel to a liquid phase. This may assist in finding optimal crystallization conditions to improve crystal yield.

Materials and Methods

An anti-VEGF stock solution of 84.4 g/L in Milli-Q® water was used with 1 M stock solutions of $ZnCl_2$ and NaOAc, pH 5.7 as ingredients for these 1 mL batch experiments. Twenty-two (22) batches were created, each with an anti-VEGF concentration of 42.2 g/L and $ZnCl_2$ and NaOAc concentrations ranging from 5 to 100 mM and 10 to 100 mM respectively (see Table 3).

The solutions were made in polypropylene tubes that were stored at ambient temperature. There were two different sets of 22 carried out, one set was not mixed, and one set was tipped over twice per day to provide gentle mixing. The tubes were observed over the course of three weeks. The percent gel formed was visually determined in the non-mixed set at the beginning and end of the three weeks. After 21 days the tubes were centrifuged and the anti-VEGF concentration in the supernatant was analyzed by A280.

Results

Table 3 shows the results of the non-mixed, or static set of 22 samples.

TABLE 3

| ZnCl$_2$ concentration (mM) | NaOAc, pH 5.7 concentration (mM) | % Gel Initial | % Gel Final | anti-VEGF concentration in supernatant (g/L) |
|---|---|---|---|---|
| 5 | 10 | 0 | 0 | 43 |
| 5 | 100 | 20 | 0 | 43 |
| 10 | 10 | 0 | 0 | 47 |
| 10 | 50 | 0 | 0 | 48 |
| 10 | 75 | 0 | 0 | 47 |
| 10 | 100 | 25 | 0 | 44 |
| 25 | 10 | 0 | 0 | 42 |
| 25 | 25 | 15 | 0 | 43 |
| 25 | 50 | 45 | 0 | 44 |
| 25 | 75 | 25 | 20 | 7.1 |
| 25 | 100 | 25 | 20 | 4.3 |
| 40 | 10 | 0 | 0 | 49 |
| 40 | 25 | 0 | 15 | 47 |
| 40 | 50 | 20 | 40 | 6.0 |
| 40 | 75 | 20 | 20 | 2.5 |
| 60 | 10 | 15 | 20 | 18 |
| 60 | 25 | 30 | 40 | 6.8 |
| 60 | 50 | 35 | 40 | 2.9 |
| 60 | 75 | 40 | 20 | 1.3 |
| 80 | 10 | 40 | 40 | 9.4 |
| 80 | 25 | 45 | 40 | 3.0 |
| 100 | 10 | 65 | 20 | 3.8 |
| 100 | 100 | 35 | 20 | 0.7 |

In the mixed set of tubes, the % gel could not be quantified because the gel phase was spread along the side of the tubes. However, a visual indication of the state of the solution, clear, gel, free solids, or gel+free solids was determined at the beginning and at the end of the 21 days. After 21 days, the tubes were centrifuged and the anti-VEGF concentration in the supernatant was analyzed by A280. Table 4 shows the results of the twice daily tipped (mixed) set of 22 samples.

TABLE 4

| ZnCl$_2$ concentration (mM) | NaOAc, pH 5.7 concentration (mM) | Observations Initial | Observations Final | anti-VEGF concentration in supernatant (g/L) |
|---|---|---|---|---|
| 10 | 50 | Clear | Free solids | 49 |
| 10 | 75 | Clear | Free solids | 48 |
| 10 | 100 | Free solids | Free solids | 47 |
| 15 | 50 | Clear | Free solids | 45 |
| 20 | 50 | Clear | Free solids | 47 |
| 25 | 25 | Clear | Free solids | 45 |
| 25 | 50 | Clear | Free solids | 42 |
| 25 | 75 | Gel | Gel + solids | 8.1 |
| 40 | 10 | Clear | Free solids | 44 |
| 40 | 25 | Gel | Gel | 20 |
| 40 | 50 | Gel | Gel | 6.5 |
| 40 | 75 | Gel | Gel | 3.2 |
| 50 | 10 | Clear | Clear | 43 |
| 50 | 25 | Gel | Gel | 11 |
| 60 | 5 | Clear | Gel | 27 |
| 60 | 10 | Gel | Gel + solids | 22 |
| 60 | 25 | Gel | Gel | 8.2 |
| 60 | 50 | Gel | Gel | 2.2 |
| 60 | 75 | Gel | Gel | 1.4 |
| 80 | 10 | Gel | Gel | 8.8 |
| 80 | 25 | Gel | Gel | 3.8 |
| 100 | 1 | Gel + solids | Gel + solids | 10 |
| 100 | 5 | Gel + solids | Gel + solids | 9.2 |
| 100 | 10 | Gel | Gel | 4.8 |

Crystals were formed in all of the tubes. Some of the crystals were free in solution and some were in a gel.

Figure 3:
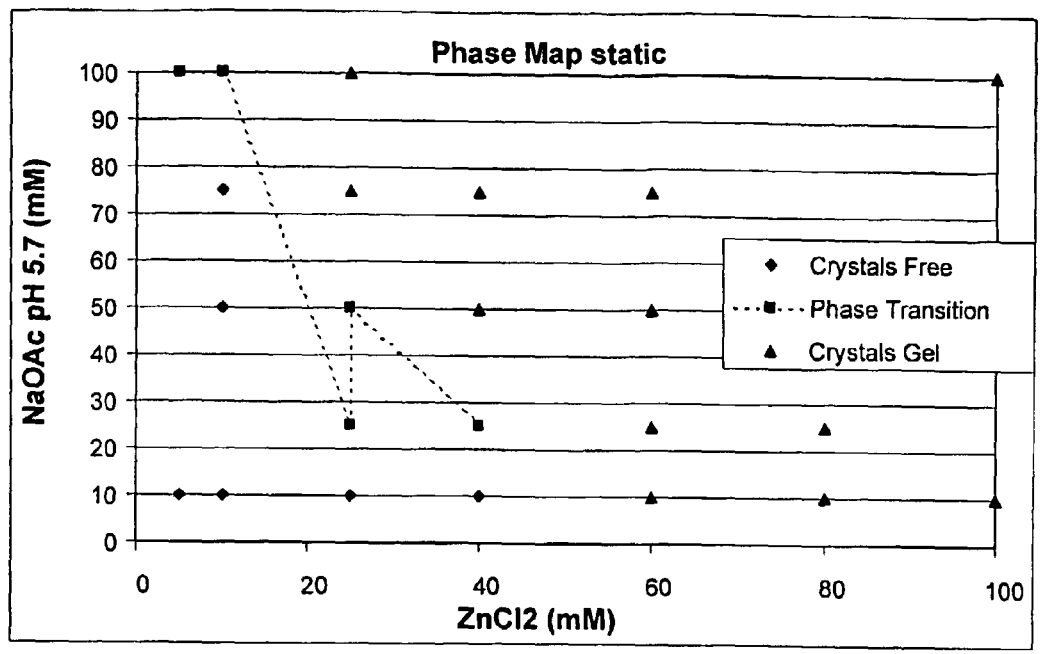
FIG. 3 shows the phase map for the static condition generated by plotting $ZnCl_2$ concentration against NaOAc concentration. The following symbols identify ♦ free crystals; ■ phase transitions; Δ gel crystals (white triangles).
Figure 4:
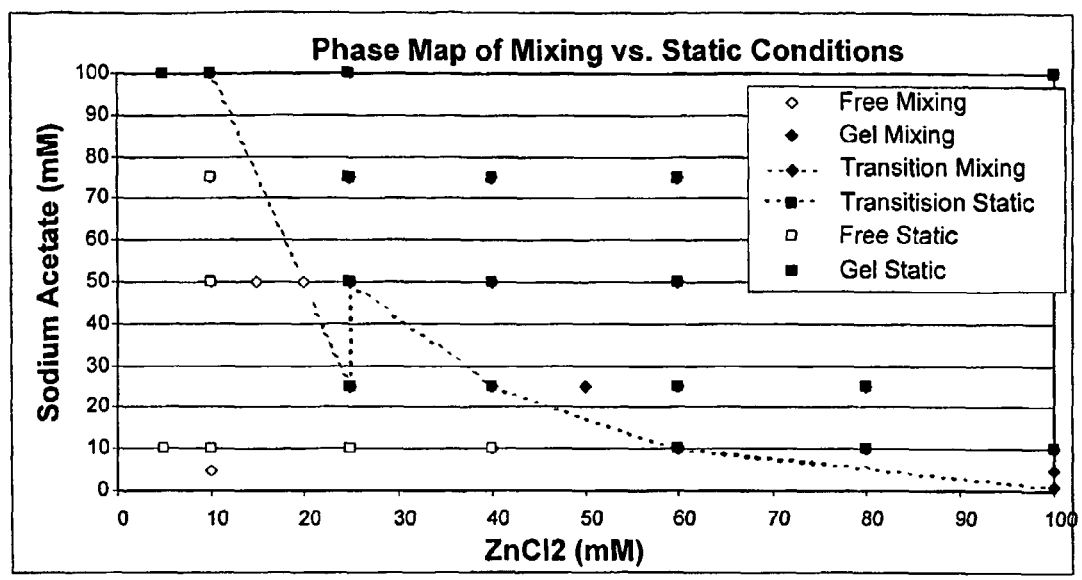
FIG. 4 shows the phase map of mixing versus static conditions. The symbols represent the following: ◇ free mixing; ♦ gel mixing; --♦-- transition mixing; --■-- transition static; □ free static; and ■ gel static.

The phase map for the non-mixed samples was generated by plotting ZnCl$_2$ concentration against NaOAc concentration. This plot can be seen in FIG. 3. FIG. 4 compares the phase maps for the mixing and non-mixing experiments.

Taken together, FIGS. 1 (from Example 1), 3 and 4 show that as the system nears the phase transition point, soluble anti-VEGF decreases to about 10-22 g/L when ZnCl$_2$ is above 40 mM and the tubes are mixing. When the tubes are static and ZnCl$_2$ concentrations are 40 mM or less, there is little to no decrease in soluble anti-VEGF concentrations. This could lead one to believe that ZnCl$_2$ is the dominant factor in the loss of soluble anti-VEGF. When the ZnCl$_2$ concentration is less than 10 mM or greater than 80 mM, the effect of NaOAc lessens. As ZnCl$_2$ concentrations near the transition points (25-60 mM), NaOAc concentrations appear to have a greater effect on the concentration of soluble anti-VEGF.

EXAMPLE 5

Crystallization of Other Antibodies

Prior art crystallization conditions for full-length antibodies typically utilize an organic precipitant such as PEG, MPD or propanol. We have discovered (see previous examples) that full-length antibodies such as anti-VEGF can be crystallized in the absence of these organic precipitants. We examined whether other full length antibodies could be crystallized with a divalent cation in the presence of NaOAc (pH 4.7; pH 5.7), HEPES (pH 7.5) or Tris (pH 9.0).

Materials and Methods

The monoclonal antibodies that were tested are: anti-HER2, anti-CD11a, anti-CD20 (C2B8) and anti-VEGF (Genentech, South San Francisco, Calif.). The preparation and characterization of an antibody with these specificities have been described in U.S. Pat. Nos. 5,736,137, 6,387,371, 6,037,454, and WO 98/45331. The antibodies were purified using three types of chromatography followed by ultrafiltration and diafiltration similar to the purification steps described in Example 1.

The monoclonal antibodies were dialyzed into Milli-Q® water to give resultant concentrations of between about 80-100 mg/mL. The experiments were performed in batch mode by combining 1 part antibody solution with 1 part of each appropriate solution. Final sample volumes were from 1 to 2 mL. The samples were stored in 6 mL polypropylene tubes.

The divalent salts that were used were ZnCl$_2$, CaCl$_2$, and MgCl$_2$. The buffers that were used had final concentrations and pH respectively of: 10 mM NaOAc, pH 4.7; 10 mM NaOAc, pH 5.7; 10 mM HEPES (4-(2-hydroxyethyl)-1-piperazineethane-sulfonic acid), pH 7.5, and 10 mM Tris (tris hydroxymethylamino-ethane), pH 9.0. The samples containing the Tris buffer solution were stored at ambient temperature, and the samples with the other buffer solutions were stored at temperatures from 2-8° C.

Samples were subjected to daily visual inspections. If no solid material was observed after 3 days of storage the temperature was radically shifted: the samples were transferred to 2-8° C. or room temperature depending on the initial storage conditions. If no solid material was observed after an additional 3 days, the samples were stored at 2-8° C. and monitored weekly. The samples with solid material were subjected to viewing under cross polarizers to determine birefringence.

Results

No crystals were observed under the conditions tested for the anti-CD40 molecule (data not shown).

The results for the anti-CD20 (C2B8) molecule with $ZnCl_2$ are shown in Table 5. Any solids observed were not crystalline based on birefrigence. However, in some cases protein gels were formed. No crystals were observed under the conditions tested for the anti-CD20 (C2B8) molecule with $CaCl_2$ and $MgCl_2$ (data not shown). N/A in the tables indicated that the absorbance of the supernatant at 280 nm was not tested.

TABLE 5

| $ZnCl_2$ (mM) | NaOAc (mM) | pH | Temperature (° C.) | Observations | Anti-CD20 (C2B8) in supernatant by A280 (g/L) |
|---|---|---|---|---|---|
| 5 | 10 | 4.7 | 2-8 | Clear | 42 |
| 10 | 10 | 4.7 | 2-8 | Clear | 42 |
| 100 | 10 | 4.7 | 2-8 | 25% gel | 13 |
| 5 | 10 | 4.7 | room | Clear | N/a |
| 10 | 10 | 4.7 | room | Clear | N/a |
| 100 | 10 | 4.7 | room | Opalescent + 20% gel | N/a |
| 5 | 10 | 5.7 | 2-8 | Clear | 42 |
| 10 | 10 | 5.7 | 2-8 | Clear | 43 |
| 100 | 10 | 5.7 | 2-8 | 75% white solid | 2.1 |
| 5 | 10 | 5.7 | room | Clear | N/a |
| 10 | 10 | 5.7 | room | Clear | N/a |
| 100 | 10 | 5.7 | room | 33% solids | N/a |

The results for the anti-HER2 molecule with $ZnCl_2$ are shown in Table 6 below. Any solids formed under the conditions shown below were not crystalline as determined by birefringence. No crystals were observed under the conditions tested for the anti-HER2 molecule with $CaCl_2$ or $MgCl_2$ (data not shown).

TABLE 6

| $ZnCl_2$ (mM) | NaOAc (mM) | pH | Temperature (° C.) | Observations | anti-HER2 in supernatant by A280 (g/L) |
|---|---|---|---|---|---|
| 5 | 10 | 4.7 | 2-8 | Clear | 51 |
| 10 | 10 | 4.7 | 2-8 | Clear | 46 |
| 100 | 10 | 4.7 | 2-8 | 25% gel | 18 |
| 5 | 10 | 4.7 | room | Clear | N/a |
| 10 | 10 | 4.7 | room | Clear | N/a |
| 100 | 10 | 4.7 | room | Opalescent | N/a |
| 5 | 10 | 5.7 | 2-8 | Clear | 46 |
| 10 | 10 | 5.7 | 2-8 | Clear | 47 |
| 100 | 10 | 5.7 | 2-8 | 60% solids | 41 |
| 5 | 10 | 5.7 | room | Clear | N/a |
| 10 | 10 | 5.7 | room | Clear | N/a |
| 100 | 10 | 5.7 | room | Gel + solids | N/a |

The results for the anti-CD11a molecule with $ZnCl_2$ are shown in Table 7 below. Any solids formed under these conditions were negative for the crystal formation as determined by birefringence. No crystals were observed under the conditions tested for the anti-CD11a molecule with $CaCl_2$ or $MgCl_2$ (data not shown).

TABLE 7

| $ZnCl_2$ (mM) | NaOAc (mM) | pH | Temperature (° C.) | Observations | anti-CD11a in supernatant by A280 (g/L) |
|---|---|---|---|---|---|
| 5 | 10 | 4.7 | 2-8 | Clear | 59 |
| 10 | 10 | 4.7 | 2-8 | Clear | N/a |
| 100 | 10 | 4.7 | 2-8 | 40% gel | 13 |
| 5 | 10 | 4.7 | room | Clear | N/a |
| 10 | 10 | 4.7 | room | Clear | N/a |
| 100 | 10 | 4.7 | room | 25% gel | N/a |
| 5 | 10 | 5.7 | 2-8 | Clear | 47 |
| 10 | 10 | 5.7 | 2-8 | Clear | 56 |
| 100 | 10 | 5.7 | 2-8 | 75% white solid | 2.3 |
| 5 | 10 | 5.7 | room | Clear | N/a |
| 10 | 10 | 5.7 | room | Clear | N/a |
| 100 | 10 | 5.7 | room | 25% gel + solids | N/a |

The results for the anti-VEGF molecule with $ZnCl_2$ are shown in Table 8 and for $MgCl_2$ in Table 9 below. Crystals and gels were formed under these conditions. Not all precipitates were positive for crystalline material by birefringent light. No crystals were observed under the conditions tested for the anti-VEGF molecule with $CaCl_2$ (data not shown).

TABLE 8

| $ZnCl_2$ (mM) | NaOAc (mM) | pH | Temperature (° C.) | Observations | anti-VEGF in supernatant by A280 (g/L) | Birefringe Crystals |
|---|---|---|---|---|---|---|
| 5 | 10 | 4.7 | 2-8 | Film | 42.8 | yes |
| 10 | 10 | 4.7 | 2-8 | Film | 43.5 | yes |
| 100 | 10 | 4.7 | 2-8 | 20% gel | 16.0 | yes |
| 5 | 10 | 4.7 | room | Film + solids | 44.2 | yes |
| 10 | 10 | 4.7 | room | Lots of solids | 42.6 | yes |
| 100 | 10 | 4.7 | room | 17% gel | 18.4 | yes |
| 5 | 10 | 5.7 | 2-8 | Film + solids | 43.9 | yes |
| 10 | 10 | 5.7 | 2-8 | Film + solids | 41.8 | yes |
| 100 | 10 | 5.7 | 2-8 | 20% gel | 4.3 | yes |
| 5 | 10 | 5.7 | room | Film | 43.1 | yes |
| 10 | 10 | 5.7 | room | Film + cloudy | 46.6 | yes |
| 100 | 10 | 5.7 | room | 17% gel | 3.8 | yes |

TABLE 9

| MgCl$_2$ (mM) | 10 mM buffer | pH | Temperature (°C.) | Observations | anti-VEGF in supernatant by A280 (g/L) |
|---|---|---|---|---|---|
| 5 | NaOAc | 4.7 | 2-8 | Clear | 51 |
| 10 | NaOAc | 4.7 | 2-8 | Clear | N/a |
| 100 | NaOAc | 4.7 | 2-8 | Clear | 52 |
| 5 | NaOAc | 4.7 | room | Clear | N/a |
| 10 | NaOAc | 4.7 | room | Clear | N/a |
| 100 | NaOAc | 4.7 | room | Clear | N/a |
| 5 | NaOAc | 5.7 | 2-8 | Clear | 51 |
| 10 | NaOAc | 5.7 | 2-8 | Clear | N/a |
| 100 | NaOAc | 5.7 | 2-8 | Clear | 50 |
| 5 | NaOAc | 5.7 | room | Clear | N/a |
| 10 | NaOAc | 5.7 | room | Clear | N/a |
| 100 | NaOAc | 5.7 | room | Clear | N/a |
| 5 | HEPES | 7.5 | 2-8 | Fine particulates | 44 |
| 50 | HEPES | 7.5 | 2-8 | Few wht ppt | 42 |
| 100 | HEPES | 7.5 | 2-8 | white particulates | 42 |
| 5 | HEPES | 7.5 | ambient | Fine particulates | 44 |
| 50 | HEPES | 7.5 | ambient | Fine particulates | 43 |
| 100 | HEPES | 7.5 | ambient | Fine particulates | 43 |
| 5 | Tris | 9.0 | 2-8 | Fine particulates | 44 |
| 50 | Tris | 9.0 | 2-8 | Fine particulates | 44 |
| 100 | Tris | 9.0 | 2-8 | Fine particulates/birefringence-small sea urchin like crystals | 51 |
| 5 | Tris | 9.0 | ambient | Fine particulates | 41 |
| 50 | Tris | 9.0 | ambient | Fine particulates/birefringence-small sea urchin like crystals | 44 |
| 100 | Tris | 9.0 | ambient | Fine particulates/birefringence-small sea urchin like crystals | 42 |

From the results above, it appears as if the combination of higher ZnCl$_2$ and NaOAc concentrations, and pHs of 4.7 and 5.7 induce changes in the phase of anti-HER2, anti-CD20 (C2B8), and anti-CD11a from soluble antibody to antibody gels. All of the ZnCl$_2$/NaOAc combinations produced crystals when added to anti-VEGF.

Only MgCl$_2$ and CaCl$_2$ were investigated at pH 7.5 and pH 9.0 (results for CaCl$_2$ not shown). Based on the results above, crystallization of anti-VEGF was observed in 10 mM Tris, 50 mM MgCl$_2$, pH 9.0 at room temperature; and in 10 mM Tris, 100 mM MgCl$_2$, pH 9.0 at both room temperature and at 2-8° C.

EXAMPLE 6

Use of Precipitants in Crystallization Conditions

We examined whether we could incorporate additives into crystallization conditions for anti-VEGF. The crystallization conditions that were used were 10 mM ZnCl$_2$ and 10 mM NaOAc, at a pH of 5.7.

Crystallization using 10 mM ZnCl$_2$ and 10 mM NaOAC at a pH of 5.7 had already been shown to produce anti-VEGF crystals. In an attempt to increase the yield, the three most effective organic precipitants (determined from screening) were added to the crystallization buffers. The precipitants that were tested were (±)-2-methyl-2,4-pentanediol (MPD) purchased from Hampton Research, polyethylene glycol (PEG) 3350 purchased from Hampton Research, and propanol purchased from Hampton Research.

Each of the precipitants was added to a polypropylene tube containing a solution of anti-VEGF (Genentech, South San Francisco, Calif.) in Milli-Q® water to give a resulting concentration of 42.4 g/L anti-VEGF, 10 mM ZnCl$_2$, 10 mM NaOAc, at a pH of 5.7, and the percentages of the precipitants given in Table 10 below.

The polypropylene tubes were placed at ambient temperature and were tipped twice per day to provide gentle mixing. After two weeks, supernatant samples were collected and the anti-VEGF concentration was analyzed by A280.

Results

The results are shown in Table 10.

TABLE 10

| Precipitant | % | Crystals | Concentration of anti-VEGF in supernatant (g/L) |
|---|---|---|---|
| PEG 3350 | 0.5 | Yes | 52 |
| PEG 3350 | 1 | Yes | 48 |
| PEG 3350 | 5 | Yes | 49 |
| Propanol | 0.5 | Yes | 41 |
| Propanol | 1 | Yes | 47 |
| Propanol | 5 | Yes | 46 |
| MPD | 0.5 | Yes | 53 |
| MPD | 1 | Yes | 48 |
| MPD | 5 | Yes | 45 |

Figure 6:
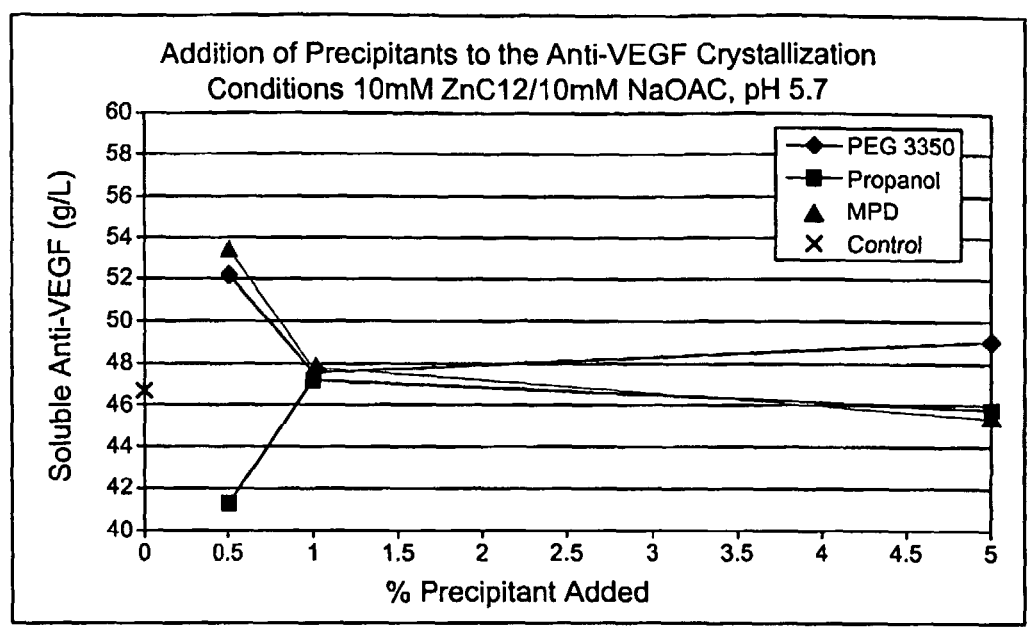
FIG. 6 shows additions of precipitants to the anti-VEGF crystallization conditions 10 mM $ZnCl_2$, 10 mM NaOAc, pH 5.7. The amount of soluble anti-VEGF was plotted against the % of precipitant added.

Crystals were visually observed in all of the batch tubes. The measured supernatant concentrations were between 41 and 53 g/L in all of the polypropylene tubes. Crystallization occurred, but did not seem to be increased by the addition of these precipitants. FIG. 6 shows the concentration of supernatant as a function of precipitant concentration for the three different precipitants. It was determined that adding MPD, PEG 3350, or propanol does not seem to significantly improve the yield over the yield using 10 mM ZnCl$_2$ and 10 mM NaOAc at pH 5.7.

EXAMPLE 7

Crystallization of Other Monoclonal Antibodies

We examined whether ZnCl$_2$ and NaOAc mixtures can be used as generic crystallization conditions for monoclonal antibodies.

The crystallization conditions that have been identified herein for anti-VEGF do not contain polyethylene glycol. All of the other conditions reported in the literature use polyethylene glycol in their crystallization process. In past experiments other antibodies have been affected by these conditions by gelling or precipitating out of solution. In this experiment, higher ZnCl$_2$ concentrations were studied in order to study the antibody's phase space and identify crystallization conditions.

Materials and Methods

The antibodies that were compared were anti-HER2, anti-CD11a, anti-2C4, anti-CD20 (2H7), anti-CD20 (C2B8), and anti-VEGF. All of the antibodies were diafiltered into Milli-Q® water and concentrated to ~100 mg/mL. The experiments were performed in batch mode, combining 1 part antibody solution with 1 part solution. The final sample volume was from about 3-5 mL, and the samples were stored in 6 mL polypropylene tubes without any protein control. The samples were stored at ambient temperature and at about 2-8° C. The samples were inspected daily. If no crystals or precipitate was observed after 3 days storage, the temperature was radically shifted: the samples were transferred to 2-8° C. or room temperature depending on the initial storage conditions. If nothing was observed after an additional 3 days, the samples were stored at about 2-8° C. and monitored weekly.

The solutions had varying concentrations of $ZnCl_2$, $CaCl_2$, and $MgCl_2$ and all had 0.01 M NaOAc and had a pH of either 4.7 or 5.7.

Results

The results for the anti-VEGF molecule in $ZnCl_2$ are shown in Table 11. Crystals were not observed using $MgCl_2$ or $CaCl_2$ under these conditions (data not shown).

TABLE 11

| $ZnCl_2$ (mM) | NaOAc (mM) | pH | Temperature (° C.) | Observations | Birefringent Crystals |
|---|---|---|---|---|---|
| 75 | 10 | 4.7 | ambient | Gel | No |
| 90 | 10 | 4.7 | ambient | Gel | 1 or 2 possible crystals |
| 120 | 10 | 4.7 | ambient | Thick gel | Gel |
| 75 | 10 | 4.7 | 2-8 | Solid gel | Small crystal |
| 90 | 10 | 4.7 | 2-8 | Solid gel | Small crystal |
| 120 | 10 | 4.7 | 2-8 | Thick gel | Crystal |
| 25 | 10 | 5.7 | ambient | Thick gel | No |
| 50 | 10 | 5.7 | ambient | Thick gel | Small gel droplets |
| 75 | 10 | 5.7 | ambient | Loose gel | Gel |
| 25 | 10 | 5.7 | 2-8 | Solid gel | Crystal |
| 50 | 10 | 5.7 | 2-8 | Solid gel | Many small crystals |
| 75 | 10 | 5.7 | 2-8 | ½ gel | Many small crystals |

The results for the anti-CD20 (C2B8) and anti-2C4 molecules did not show formation of crystals or gels under any of the conditions tested (data not shown).

The results for the anti-CD20 (2H7) molecule are shown in Table 12 ($ZnCl_2$), Table 13 ($CaCl_2$), and Table 14 ($MgCl_2$) below. In many cases, protein gels were formed. Precipitated material was not crystalline as determined by birefringence.

TABLE 12

| $ZnCl_2$ (mM) | NaOAc (mM) | pH | Temperature (° C.) | Observations | Birefringent Crystals |
|---|---|---|---|---|---|
| 75 | 10 | 4.7 | ambient | Clear | No |
| 90 | 10 | 4.7 | ambient | Thin gel | No |
| 120 | 10 | 4.7 | ambient | Gel | No |
| 75 | 10 | 4.7 | 2-8 | Ppt | No |
| 90 | 10 | 4.7 | 2-8 | Ppt | No |
| 120 | 10 | 4.7 | 2-8 | Ppt | No |
| 25 | 10 | 5.7 | ambient | Granular ppt | No |
| 50 | 10 | 5.7 | ambient | Ppt | No |
| 75 | 10 | 5.7 | ambient | Ppt | No |
| 25 | 10 | 5.7 | 2-8 | Gel | No |
| 50 | 10 | 5.7 | 2-8 | Thick gel | No |
| 75 | 10 | 5.7 | 2-8 | Thick gel | No |

TABLE 13

| $CaCl_2$ (mM) | NaOAc (mM) | pH | Temperature (° C.) | Observations | Birefringent Crystals |
|---|---|---|---|---|---|
| 200 | 10 | 4.7 | ambient | Opalescent, white solids | no |
| 500 | 10 | 4.7 | ambient | Gel | no |
| 200 | 10 | 4.7 | 2-8 | Opalescent thick gel | no |
| 500 | 10 | 4.7 | 2-8 | Opalescent thick gel | no |
| 200 | 10 | 5.7 | ambient | Thick gel | no |
| 500 | 10 | 5.7 | ambient | Opalescent thick gel | no |
| 200 | 10 | 5.7 | 2-8 | Thick gel | no |
| 500 | 10 | 5.7 | 2-8 | Thick gel | no |

TABLE 14

| $MgCl_2$ (mM) | NaOAc (mM) | pH | Temperature (° C.) | Observations | Birefringent Crystals |
|---|---|---|---|---|---|
| 200 | 10 | 4.7 | ambient | Brief gel | no |
| 500 | 10 | 4.7 | ambient | Thick gel | no |
| 200 | 10 | 4.7 | 2-8 | Thick gel | no |
| 500 | 10 | 4.7 | 2-8 | Thick gel | no |
| 200 | 10 | 4.7 | ambient | Brief gel | no |
| 500 | 10 | 4.7 | ambient | Thick gel | no |
| 200 | 10 | 5.7 | 2-8 | Thick gel | no |
| 500 | 10 | 5.7 | 2-8 | Thick gel | no |

The results for the anti-HER2 molecule are shown in Table 15 ($ZnCl_2$) below. Crystals were not observed using $MgCl_2$ or $CaCl_2$ under these conditions (data not shown).

TABLE 15

| $ZnCl_2$ (mM) | NaOAc (mM) | pH | Temperature (° C.) | Observations | Birefringent Crystals |
|---|---|---|---|---|---|
| 75 | 10 | 4.7 | Ambient | Light milky | No |
| 90 | 10 | 4.7 | Ambient | Light milky | No |
| 120 | 10 | 4.7 | Ambient | Opalescent | No |
| 75 | 10 | 4.7 | 2-8 | Clear | No |
| 90 | 10 | 4.7 | 2-8 | Opalescent | No |
| 120 | 10 | 4.7 | 2-8 | Small solid particles | Weakly birefringent |
| 25 | 10 | 5.7 | ambient | Light milky | No |
| 50 | 10 | 5.7 | ambient | Light milky | No |
| 75 | 10 | 5.7 | ambient | Gel | No |
| 25 | 10 | 5.7 | 2-8 | Clear | No |
| 50 | 10 | 5.7 | 2-8 | Gel | No |
| 75 | 10 | 5.7 | 2-8 | Soft gel | No |

The results for the anti-CD11a molecule are shown in Table 16 ($ZnCl_2$) below. Crystals were not observed using $MgCl_2$ or $CaCl_2$ under these conditions (data not shown).

TABLE 16

| $ZnCl_2$ (mM) | NaOAc (mM) | pH | Temperature (° C.) | Observations | Birefringent Crystals |
|---|---|---|---|---|---|
| 75 | 10 | 4.7 | ambient | Clear | No |
| 90 | 10 | 4.7 | ambient | Clear | No |
| 120 | 10 | 4.7 | ambient | Opalescent | No |
| 75 | 10 | 4.7 | 2-8 | Clear | No |
| 90 | 10 | 4.7 | 2-8 | Clear | No |
| 120 | 10 | 4.7 | 2-8 | Ppt | No |
| 25 | 10 | 5.7 | ambient | Clear | No |
| 50 | 10 | 5.7 | ambient | Clear | No |
| 75 | 10 | 5.7 | ambient | Gel/solid | No |
| 25 | 10 | 5.7 | 2-8 | Clear | No |
| 50 | 10 | 5.7 | 2-8 | Opalescent | No |
| 75 | 10 | 5.7 | 2-8 | Ppt | No |

These results show that different antibodies can either form crystals or gels when contacted with $ZnCl_2$ and NaOAc.

We claim:

1. A method for producing crystals of an anti-VEGF antibody comprising: a) contacting said anti-VEGF antibody with a solution that comprises about 5 to 120 mM $ZnCl_2$ and about 1 to 100 mM sodium acetate buffer at a pH of about 4.7 to 5.7; and b) incubating the anti-VEGF antibody and the solution until crystals of the antibody are formed, wherein said anti-VEGF antibody is bevacizumab.

2. The method of claim 1, wherein the ZnCl$_2$ is about 10 mM to 80 mM.

3. The method of claim 2, wherein the ZnCl$_2$ is about 25 mM to 60 mM.

4. The method of claim 1, wherein the buffer comprises about 1 mM to 20 mM NaOAc.

5. The method of claim 1, wherein the buffer comprises about 25 mM to 75 mM NaOAc.

6. The method of claim 1, wherein the solution comprises more than about 10 mM ZnCl2 and more than about 5 mM NaOAc.

7. The method of claim 6, wherein the solution comprises about 100 mM ZnCl2 and about 10 mM NaOAc.

8. The method of claim 1, wherein the contacting is at ambient temperature.

9. A method for producing crystals of an anti-VEGF antibody comprising: a) contacting said anti-VEGF antibody with a solution that comprises about 5 to 100 mM MgCl$_2$ and about 1 to 100 mM Tris buffer at a pH of about 9.0; and b) incubating the anti-VEGF antibody-and the solution until crystals of the antibody are formed, wherein said anti-VEGF antibody is bevacizumab.

10. The method of claim 9, wherein the Tris buffer is about 10 mM.

11. The method of claim 9, wherein the MgCl$_2$ is about 50 mM to 100 mM.

12. The method of claim 9, wherein the contacting is at 2-8° C.

13. The method of claim 9, wherein the contacting is at ambient temperature.

* * * * *